US008530453B2

(12) United States Patent
Sucholeiki

(10) Patent No.: US 8,530,453 B2
(45) Date of Patent: Sep. 10, 2013

(54) COMPOUNDS AND METHODS FOR THE TREATMENT OF PAIN AND OTHER DISEASES

(75) Inventor: Irving Sucholeiki, Winchester, MA (US)

(73) Assignee: Aquilus Pharmaceuticals, Inc., Winchester, MA (US)

( * ) Notice: Subject to any disclaimer, the term of this patent is extended or adjusted under 35 U.S.C. 154(b) by 246 days.

(21) Appl. No.: 12/924,214

(22) Filed: Sep. 23, 2010

(65) Prior Publication Data

US 2011/0230452 A1    Sep. 22, 2011

Related U.S. Application Data

(60) Provisional application No. 61/277,657, filed on Sep. 28, 2009.

(51) Int. Cl.
| | |
|---|---|
| *A01N 37/18* | (2006.01) |
| *A01N 43/40* | (2006.01) |
| *A61K 31/65* | (2006.01) |
| *A61K 31/44* | (2006.01) |
| *C07D 209/00* | (2006.01) |

(52) U.S. Cl.
USPC ........................ 514/152; 548/452; 514/347

(58) Field of Classification Search
USPC ................... 514/152, 347; 548/452
See application file for complete search history.

(56) References Cited

U.S. PATENT DOCUMENTS

| 5,886,022 A | 3/1999 | Kluender | |
|---|---|---|---|
| 7,420,001 B2 | 9/2008 | Levin | |
| 2003/0225043 A1* | 12/2003 | Watanabe et al. ............ | 514/150 |
| 2008/0221195 A1 | 9/2008 | Wortmann | |
| 2008/0261994 A1 | 10/2008 | Inaba et al. | |

FOREIGN PATENT DOCUMENTS

| WO | 20060036928 A2 | 4/2006 |
|---|---|---|
| WO | 2010075287 A2 | 7/2010 |

OTHER PUBLICATIONS

Wolff et. al., "Burger's Medicinal Chemistry and Drug Discovery," 5th Ed. Part 1, pp. 975-977 (1995).*
Banker, Gilbert S. et al., Modem Pharmaceutics, Marcel Dekker, New York, 1996.*
A.M. Rouhi, Chem. & Eng. News, Feb. 24, 2003, 81(8), 32-35.*
Morissette et al. Adv. Drug Delivery Rev. 2004, 56,275-300.*
Ramnath (Matrix Metalloproteinase Inhibitors, 2004, p. 96-102).*
Sommer, C.; A metalloprotease-inhibitor reduces pain associated behavior in mice with experimental neuropathy, Neurosci Lett. 1997; 45-48, vol. 237.
Kawasaki, Y.; Distinct roles of matrix metalloproteases in the early- and late-phase development of neuropathic pain, Nature Medicine, 2008, 331-336, vol. 14(3).
Kobayashi, H.; MMPs initiate Schwann cell-mediated MBP degradation and mechanical nociception after nerve damage, Molecular & Cellular Neuroscience, 2008, 619-627, vol. 39.
Komori, K.; Absence of mechanical allodynia and Aβ-fiber sprouting after sciatic nerve injury in mice lacking membrane-type 5 matrix metalloproteinase, FEBS Lett., 2004, 125-128, vol. 557.
Liu, W.T.; Spinal matrix metalloproteinase-9 contributes to physical dependence on morphine in mice, Journal of Neuroscience, 2010, 7613-7623, vol. 30(22).
Kushner, D.J.; Pharmacological uses and perspectives of heavy water and deuterated compounds, Can. J. Physiol Pharmacol, 1999, 79-88, vol. 77(2).
Schneider, F.; Enhanced plasma concentration by selective deuteration of rofecoxib in rats, Arzneimittelforschung. [BiRDS Pharma GmbH] 2006, p. 295-300, vol. 56(4).
Hirota, M.; Isomerism and polymorphism of cinnamic acids and deuterated allocinnamic acids, Bulletin of the Chemical Society of Japan, 1959, 703-706, vol. 32(7).
Lin, H.O., Polymorphism in sulfanilamide-d4, Journal of Pharmaceutical Science, 2006, 972-979, vol. 59(7).
Crawford, S.; Isotopic Polymorphism in Pyridine, Angewandte Chemie International Edition, 2009, 755-757, vol. 48 (4).
Chiappori, A.A.; A Phase I Pharmacokinetic and Pharmacodynamic Study of S-3304,a Novel Matrix Metalloproteinase Inhibitor, in Patients with Advanced and Refractory SolidTumors, Clin. Cancer Res. 2007, 2091-2099, vol. 13(7).
Ikejiri, M.; Potent mechanism-based inhibitors for matrix metalloproteinases, Journal of Biological Chem., 2005, 33992, vol. 280.
France, S.; Performing the Synthesis of a Complex Molecule on Sequentially Linked Columns: Toward the Development of a Synthesis Machine, Organic Letters, 2005, 3009, vol. 7(14).
Rudek, M.; Phase I Clinical Trial of Oral COL-3, a Matrix Metalloproteinase Inhibitor, in Patients With Refractory Metastatic Cancer, J. Clinical Oncology, 2001,584-592, vol. 19.
Chung, Y.J.; 5-Carboxylate Substituted Piperazine-2-ones as Potent and Selective MMP-2 Inhibitors, Bull. Korean Chem. Soc., 2008, 1103-1104, vol. 29(6).
Tamura, Y.; Highly Selective and Orally Active Inhibitors of Type IV Collagenase (MMP-9 and MMP-2): N-Sulfonylamino Acid Derivatives, J. Med. Chem., 1988, 640-649, vol. 41.
Kleifeld, O.; X-ray absorption studies of human matrix metalloproteinase-2 (MMP-2) bound to a highly selective mechanism-based inhibitor. comparison with the latent and active forms of the enzyme, Journal of Biological Chem., 2001,17126, vol. 276.
Whittaker, M.; Design and therapeutic application of matrix metalloproteinase inhibitors, Chem. Rev., 1999, 2735-2776, vol. 99(9).
Golub, L.M.; A non-antibacterial chemically-modified tetracycline inhibits mammalian collagenase activity, Journal of Dental Research, 1987, 1310-1314, vol. 66(8).

(Continued)

Primary Examiner — Sreeni Padmanabhan
Assistant Examiner — Uma Ramachandran
(74) Attorney, Agent, or Firm — Burns & Levinson LLP; Jacob N. Erlich

(57) ABSTRACT

The present invention relates generally to pharmaceutical agents, and in particular, to metalloprotease inhibitor compounds. More particularly, the present invention provides a new class of dual acting MMP-2 and MMP-9 inhibiting compounds that exhibit increased potency, metabolic stability and/or reduced toxicity in relation to currently known MMP-2 and MMP-9 inhibitors for the treatment of pain and other diseases. Additionally, the present invention relates to methods for treating pain, addiction and/or withdrawal symptoms in a patient comprising administering to the patient a pain-reducing effective amount of a present compound.

8 Claims, No Drawings

(56) References Cited

OTHER PUBLICATIONS

Green, A.; Chemistry of the Tetracycline Antibiotics. III. 12a-Deoxytetracycline, Journal of the American Chemical Society, 1960, 3950-3953, vol. 82(15).

Yoshida, T.; Activation of water molecule. 2. Generation of strong hydroxo bases by the reaction of water with platinum(0) phosphine complexes and the applications as catalysts for hydrogen-deuterium exchange and hydration reactions, . Journal of the American Chemical 5 Society, 1979, 2027-2038, vol. 101(8).

Fisher, L.E.; From Bench to Pilot Plant-Process Research in the Pharmaceutical Industry, ACS Symposium Series, (Apr. 19, 2002), pp. 89-100, vol. 817, Chapter 6.

Bennet, G.J.; A peripheral mononeuropathy in rat that produces disorders of pain sensation like those seen in man, Pain, 1988, 87-107, vol. 33.

Kim, S.H.; An experimental model for peripheral neuropathy produced by segmental spinal nerve ligation in the rat, Pain, 1992, 355-363, vol. 50.

Hylden, J.L.; Intrathecal morphine in mice: A new technique, Eur. J Pharmacol., 1980, 313-316, vol. 67.

Chaplan, S.R.; Quantitative assessment of tactile allodynia in the rat paw, Journal of Neuroscience Methods, 1994, 55-63, vol. 53.

Dixon, W.J.; Efficient Analysis of Experimental Observations, Annual Review Pharmacology Toxicology, 1980, 441-462, vol. 20.

Labuda, C.J.; Low dose aspirin attenuates escape/avoidance behavior, but does not reduce mechanical hyperalgesia in a rodent model of inflammatory pain, Neuroscience Letters, 2001, 137-140, vol. 304, Issue 3.

Zachariou, V.; Essential role for RGS9 in opiate action, Proc Natl Acad Sci U S A, 2003, p. 13656-13661, vol. 100.

Liu, W.T.; EphB receptor signaling in mouse spinal cord contributes to physical dependence on morphine, Faseb J., 2009, p. 90-98, vol. 23.

Knight, C.G, A novel coumarin-labelled peptide for sensitive continuous assays of the matrix metalloproteinases, FEBS LETT., 1992, 263-266, vol. 296(3).

Bickett, D.M.; A High Throughput Fluorogenic Substrate for Interstitial Collagenase (MMP-1) and Gelatinase (MMP-9), Analytical Biochemistry, 1993, 58-64, vol. 212.

\* cited by examiner

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
```

```
<223> OTHER INFORMATION: Chemically synthesized
<220> FEATURE:
<221> NAME/KEY: MOD_RES
<222> LOCATION: (1)..(1)
<223> OTHER INFORMATION: Lys at position 1 modified with N-Me-2-
      aminobenzoyl
<220> FEATURE:
<221> NAME/KEY: MOD_RES
<222> LOCATION: (4)..(4)
<223> OTHER INFORMATION: METHYLATION
<220> FEATURE:
<221> NAME/KEY: MISC_FEATURE
<222> LOCATION: (6)..(6)
<223> OTHER INFORMATION: Xaa at position 6 is Cha, defined as
      13-cyclohexylalanyl

<400> SEQUENCE: 1

Lys Ala His Cys Gly Xaa Pro
1               5
```

COMPOUNDS AND METHODS FOR THE TREATMENT OF PAIN AND OTHER DISEASES

CROSS-REFERENCE TO RELATED APPLICATIONS

This application is a based on provisional U.S. Application No. 61/277,657 that was filed on 28 Sep. 2009, the contents of which are hereby incorporated by reference.

FIELD OF THE INVENTION

The present invention relates generally to metalloprotease inhibiting compounds, and more particularly to MMP-2 and/or MMP-9 inhibiting compounds and their use for treating pain, drug addiction, opioid withdrawal and other diseases.

BACKGROUND OF THE INVENTION

Inflammation is defined as the complex biological response of vascular tissues to harmful stimuli, such as pathogens, damaged cells, or irritants. It is a protective attempt by the organism to remove the injurious stimuli as well as initiate the healing process for the tissue. Inflammation may be acute (early phase of response) or chronic (occurs over a long time). Acute inflammation involves polymorphonuclear neutrophil leukocytes while chronic inflammation involves monocytes, macrophages, lymphocytes and plasma cells (collectively, mononuclear leukocytes). One affect of both acute and chronic inflammation is the sensation of pain which can be either neuropathic or nociceptive. Some common ailments associated with neuropathic pain are lower back pain, neuralgia/fibromyalgia, diabetic neuropathic pain and pain associated with multiple sclerosis. Common ailments associated with nociceptive pain are arthritic pain, particularly osteoarthritis and rheumatoid arthritis, post-operative pain, cancer-related pain and HIV-related pain.

In 1997 the research group of Sommer and coworkers (Sommer C, Schmidt C, George A, Toyka K V. Neurosci Lett. 1997; 237: 45-48) showed that epineural injection of a potent matrix metalloproteinase inhibitor (TAPI-0) in the chronic constriction injury (CCI)-mouse model was able to block both mechanical allodynia and thermal hyperalgesia after the third day of daily injections. At the time the authors concluded that inhibition of TNF-alpha was the mechanism of action since the inhibitor (TAPI-0) was a known inhibitor of TNF-alpha (IC50~100 nM). However, subsequently it has been shown that TABI-0 has a IC50 for MMP-9 of 0.5 nM.

Ji and coworkers (Nature Medicine 14 (13), (2008), 331-336) have recently found that matrix metalloproteinase-9 (MMP-9) was upregulated in injured dorsal root ganglion (DRG) primary sensory neurons in the early phase of the L5 spinal nerve ligation (SNL) neurophathic pain model (first day and then declining after $3^{rd}$ day) and that matrix metalloproteinase-2 (MMP-2) had a delayed response in the model (upregulation starting from day 7 and still present on day 21). They also found that MMP-2 induces neuropathic pain by IL-1β cleavage and astocytic extracellular signal-regulated kinase (ERK) activation. They also found that endogenous matrix metalloproteinase inhibitors (TIMP-1 and TIMP-2) also suppressed neuropathic pain in the model. Kobayashi and coworkers (Molecular and Cellular Neuroscience, 39, (2008), 619-627) recently demonstrated that MMPs degrade peripheral myelin basic protein (MBP) and that a broad spectrum, hydroxamic acid containing MMP inhibitor (GM6001) was found to attenuate mechanical nociception. There have been other studies by other groups using knock out mice (Komori K., et al. FEBS Lett., 557: 125-128, (2004) and Folguera, A.; et. al PNAS, 106(38), 16451-16456 (2009)) demonstrating that MMP-2 is critical for inducing chronic neuropathic pain.

Among chronic users of opioids both tolerance and hyperalgesia frequently occur. Tolerance is a state of adaptation in which exposure to the opioid induces changes that result in a lowering of the drug's pain blocking effects over time. The result of tolerance is that the user requires higher dosages of the opioid to maintain a therapeutic effect. Hyperalgesia is a state in which exposure to the opioid sensitizes the user to pain. Patients who chronically use opioids such as morphine become not only sensitize to the original pain but in many cases report new types of pain while on the opioid itself. Both tolerance and hyperalgesia are factors that help explain opioids prevalence for addiction among chronic users. Recently, Song and coworkers (The Journal of Neuroscience, 30(22), (2010), 7613-7623) found a strong link between the physical dependence due to opioid withdrawal and enhanced MMP-9 activity in the dorsal horn. These researchers found that by administering exogenous MMP-9 in the spine they could induce both morphine-like withdrawal behavior as well as mechanical allodynia in normal mice. When the researchers injected intrathecally a MMP-9 inhibitor (2-[Benzyl-(4-methoxy-benzenesulfonyl)-amino]-5-diethylamino-N-hydroxy-3-methyl-benzamide) in mice undergoing morphine withdrawal they could eliminate the withdrawal behaviors. When they co-administered either a MMP-2 or a MMP-9 inhibitor they could significantly reduce morphine tolerance in mice. The compounds that had been used in all of the above studies to block either MMP-2 and/or MMP-9 activity were hydroxamic acid containing MMP inhibitors that have known toxic side-effects.

Matrix metalloproteinases (MMPs) are a family of structurally related zinc-containing enzymes that have been reported to mediate the breakdown of connective tissue in normal physiological processes such as embryonic development, reproduction, and tissue remodelling. Over-expression of MMPs or an imbalance between MMPs has been suggested as factors in inflammatory, malignant and degenerative disease processes characterized by the breakdown of extracellular matrix or connective tissues. MMPs are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis but not pain. MMP-2 (72 kDa gelatinase/GelatinaseA) and MMP-9 (92 kDa gelatinase/GelatinaseB) degrade the extracelluar matrix components of the basement membrane. Their substrates include types IV and V collagen, fibronectin, elastin, and denatured interstitial collagens. Matrix degradation attributed to this proteinase has been shown to play an important role in the progression of such diseases as atheroslerosis, inflammation, stroke, and tumor growth and metastasis. However until recently, there has not been very much scientific literature published on the use of MMP-2 and/or MMP-9 inhibitors to treat pain and/or addiction.

Matrix metalloproteinase have been tested clinically in a few indications. Most predominantly in arthritis and cancer. Inhibitors that have entered clinical trials specifically for an oncologic indication include prinomastat (AG3340; Agouron/Pfizer), BAY 12-9566 (Bayer Corp.), batimistat (BB-94; British Biotech, Ltd,), BMS-275291 (formerly D2163; Celltech/Bristol-Myers Squibb), marimastat (BB 2516; British Biotech, Ltd./Schering-Plough), MMI270(B) (formerly CGS-27023A; Novartis), and Metastat (COL-3; CollaGenex). Many of the hydroxamic acid containing inhibitors exhibit very broad toxicities in humans. For example, Marimastat, which contains a hydroxamate moiety, exhibited time-dependent and dose-dependent musculoskeletal toxicities (arthralgia, myalgia, tendinitis) in humans. Other toxicities for marimastat include ascites, disseminated carcinoma, chills, cholangitis, dizziness, dyspnea, edema, fatigue, fever, gastrointestinal (anorexia, nausea, vomiting, diarrhea, constipation), gastrointestinal hemorrhage, headache, heartburn, hepatic toxicity, hypercalcemia, hyperglycemia, rash, and shortness of breath. It is not known whether the toxicities exhibited by many of the MMP inhibitors are attributed to the hydroxamic acid moiety contained in many of these broad spectrum MMP inhibitors, however, it is clear that having an MMP inhibitor that does not contain a hydroxamic acid group could reduce some of the potential metabolic liabilities.

Kushner and coworkers (Kushner, D. J.; Baker, A.; Dunstall, T. G. Can J. Physiol Pharmacol, 77(2), (1999) p. 79-88) have presented examples of how incorporating deuterium into a drug can often reduce the level of metabolic induced transformations especially those mediated by Cytochrome P450. This reduce rate of Cytochrome P450 induce metabolism can sometimes translate directly to enhanced bioavailability. The reason for this is due to the fact that atomic substitution of a hydrogen by a deuterium in a drug alters the strength of the carbon-deuterium bond of the drug, while keeping it's 3D surface very similar to that of the nondeuterated version. Substitution of deuterium for hydrogen, can give rise to an isotope effect that can alter the pharmacokinetics of the drug. In a reaction in which the cleavage of a C—H bond is rate determining the same reaction of the C-D analogue will be reduced. For example Schneider and coworkers (Scheneider, F.; et al., BiRDS Pharma GmbH, Arzneimittel Forschung (2006), 56(4), p. 295-300) have shown that replacing several of the hydrogen atoms around one of the aromatic rings of the COX-2 inhibitor Refecoxib (4-(4-methylsulfonylphenyl)-3-phenyl-5H-furan-2-one) with deuterium (at positions 2',3', 4',5' an 6') enhanced the oral bioavailability of the drug without affecting it's COX-2 selectivity. If one applied this strategy to the tryptophan based acid S-3304 one could reduce its susceptibility to cytochrome P-450 hdyroxylation and ultimately enhance its overall bioavailability and possibly it's target tissue compound concentration.

Another possible affect of incorporating deuterium into a drug is on its polymorphic (i.e., different crystalline forms) properties. For example, Hirota and Urushibara (Bulletin of the Chemical Society of Japan, 32(7), (1959), 703-706) have shown that replacing a single vinylic hydrogen for deuterium on Allocinnamic acid can change both the melting point and the intensity of the x-ray diffraction pattern of the molecule. Lin and Guillory (Journal of Pharmaceutical Science, Vol. 59(7), (2006), 972-979) have shown that sulfanilamide-d4 exhibited smaller heats of transition and heats of fusion for its various crystalline states as compared to it's corresponding non-deuterated forms. Finally, Crawford and co-workers (Crawford, S. et al., Angewandte Chemie International Edition, 48(4), (2009), 755-757) recently showed that the crystalline form of fully deuterated pyridine adopts a unique configuration that can only be obtained under high pressure with the non-deuterated parent. Their work clearly showed that replacing hydrogen for deuterium changes the strength of interaction between various atoms in neighboring molecules causing a change in the crystalline arrangement to one that is more energetically favorable. This change in crystalline arrangement or polymorph may allow for improved dissolution properties and enhanced bioavailability.

Sucholeiki (WO/2010/075287) has shown that partially deuterating a matrix metalloproteinase (MMP) inhibitor can enhance the bioavailability of that inhibitor as compared it's non-deuterated parent. In human blood, the MMP inhibitor S3304 was known to form several hydroxylated metabolites (Chiappori, A. A. et al. Clin. Cancer Res. 2007, 13(7), 2091-2099). Two of the main metabolites involved hydroxylation around the indole ring of the tryptophan moiety and a third involved hydroxylation of the toluene methyl portion of the S3304 molecule. When the terminal toluene methyl portion of S3304 was deuterated, the compound was observed to exhibit greater in-vivo biological activity in the spinal nerve ligation (SNL) mouse model for mechanical allodynia as compared to vehicle control and non-deuterated parent (S3304).

There are a few non-hydroxamic acid containing MMP inhibitors that have appeared in the literature, a much smaller set of these have been tested clinically in cancer and/or inflammation. None of these, however, have been tested against pain or to reduce the tolerance and withdrawal associated with opioid use in animal models or humans. A series of MMP-2 and/or MMP-9 inhibiting compounds is presented and a method for their use in inhibiting pain and other diseases is disclosed.

SUMMARY OF THE INVENTION

The present invention relates to a new method for treating pain and/or for reducing the tolerance and withdrawal side-effects due to opioid use utilizing a MMP-2 and/or a MMP-9 inhibitor.

The MMP-2 and/or MMP-9 inhibitor is represented by the general Formulas (I-XIII):

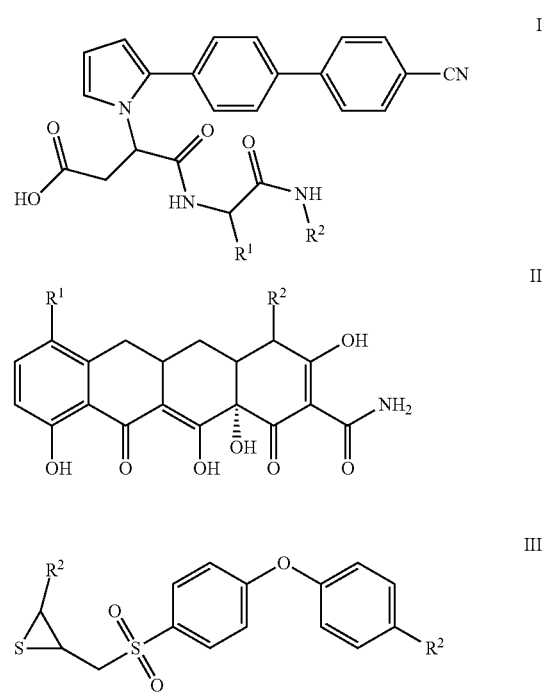

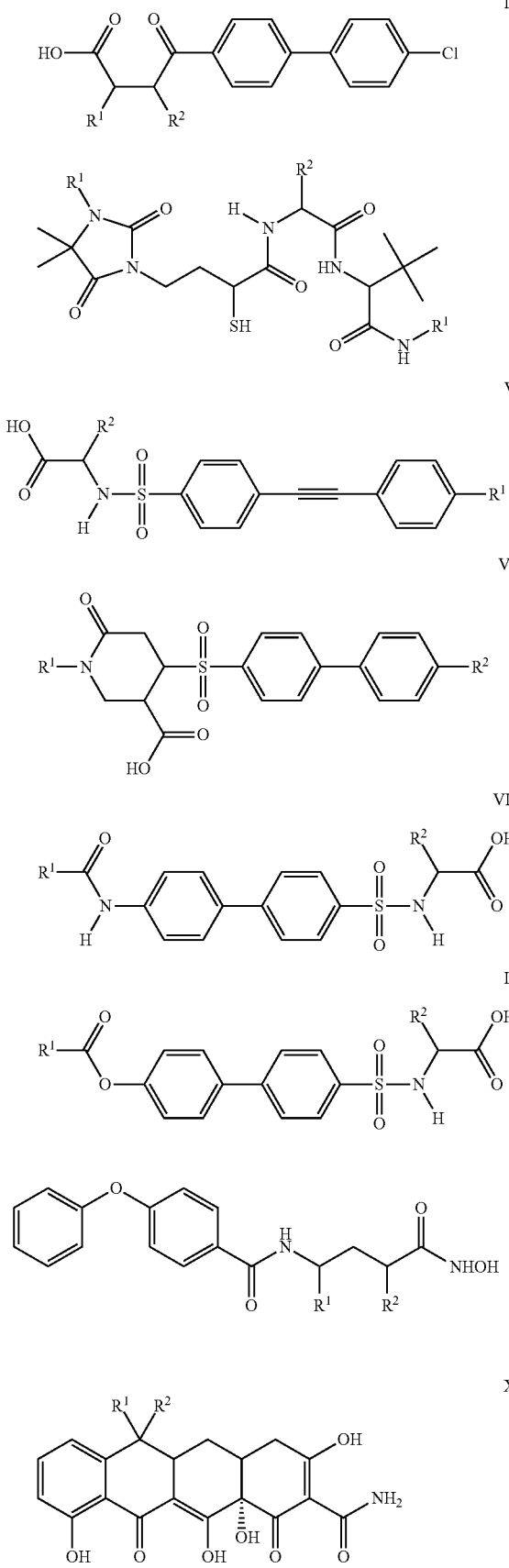

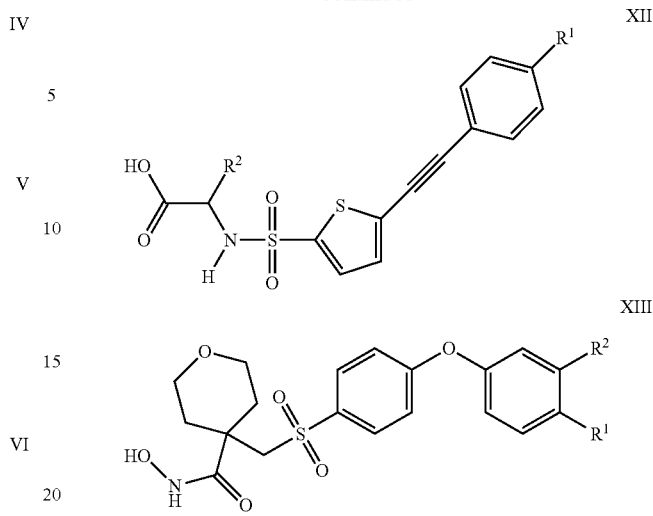

wherein all variables in the preceding Formulas (I-XIII) are as defined herein below.

$R^1, R^2$ is independently selected from the group consisting of hydrogen, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, hydroxy, alkoxy, aryl, heteroaryl, arylalkyl, heteroarylalkyl, alkenyl, alkynyl, $NO_2$, $NR^9R^9$, $NR^9NR^9R^9$, $NR^9N=CR^9R^9$, $NR^9SO_2R^9$, CN, $C(O)OR^9$, and fluoroalkyl, wherein alkyl, cycloalkyl, alkoxy, alkenyl, alkynyl and fluoroalkyl are optionally substituted one or more times and heterocycloalkyl fused heteroarylalkyl are optionally substituted one or more times;

N-oxides, deuterated analogs, pharmaceutically acceptable salts, prodrugs, formulations, polymorphs, tautomers, racemic mixtures or stereoisomers thereof.

The MMP-2 and/or MMP-9 inhibiting compounds of the present invention may be also be used in the treatment of other metalloprotease mediated diseases, such as rheumatoid arthritis, osteoarthritis, abdominal aortic aneurysm, cancer, inflammation, atherosclerosis, multiple sclerosis, chronic obstructive pulmonary disease, ocular diseases, neurological diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimer's disease, arterial plaque formation, periodontal, viral infection, stroke, cardiovascular disease, reperfusion injury, trauma, chemical exposure or oxidative damage to tissues, wound healing, haemorrhoid, skin beautifying and pain.

In particular The MMP-2 and/or MMP-9 inhibiting compounds of the present invention may be used in the treatment of pain, opioid tolerance and/or withdrawal side-effect due to opioid use in a patient, said method comprising the step of administering to the patient an effective amount of a present compound in combination with a carrier, wherein the patient is suffering from enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to viral infection, e. g., HIV, post-polio syndrome, and post-herpetic neuralgia; phantom limb pain; labor pain; cancer pain; post-chemotherapy pain; post-stroke pain; post-operative pain; physiological pain; inflammatory pain; acute inflammatory conditions/visceral pain, e. g., angina, irritable bowel syndrome (IBS), and inflammatory bowel disease; neuropathic pain; neuralgia; painful diabetic neuropathy; traumatic nerve injury; spinal cord injury; and tolerance to narcotics or withdrawal from narcotics.

The present invention also provides MMP-2, MMP-9 and/or other metalloprotease inhibiting compounds that are useful as active ingredients in pharmaceutical compositions for treatment or prevention of metalloprotease—especially MMP-2 and/or MMP-9-mediated diseases. The present invention also contemplates use of such compounds in pharmaceutical compositions for oral or parenteral administration, comprising one or more of the MMP-2 and/or MMP-9 inhibiting compounds disclosed herein.

The present invention further provides methods of inhibiting MMP-2, MMP-9 and/or other metalloproteases, by administering formulations, including, but not limited to, oral, rectal, topical, intrathecal, intravenous, parenteral (including, but not limited to, intramuscular, intravenous), ocular (ophthalmic), transdermal, inhalative (including, but not limited to, pulmonary, aerosol inhalation), nasal, sublingual, subcutaneous or intraarticular formulations, comprising the heterobicyclic metalloprotease inhibiting compounds by standard methods known in medical practice, for the treatment of diseases or symptoms arising from or associated with metalloprotease, especially MMP-2 and including prophylactic and therapeutic treatment. Although the most suitable route in any given case will depend on the nature and severity of the conditions being treated and on the nature of the active ingredient. The compounds from this invention are conveniently presented in unit dosage form and prepared by any of the methods well known in the art of pharmacy.

The MMP-2 and/or MMP-9 inhibiting compounds of the present invention may be used in combination with a disease modifying antirheumatic drug, a nonsteroidal anti-inflammatory drug, a COX-2 selective inhibitor, a COX-1 inhibitor, an immunosuppressive, a steroid, a biological response modifier or other anti-inflammatory agents.

DETAILED DESCRIPTION OF THE INVENTION

The term "D" as used herein alone or as part of a chemical structure or group, denotes deuterium.

The term "deuterated" as used herein alone or as part of a group, denote optionally substituted deuterium atoms.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "heteroalkyl" and which may be used interchangeably with the term "alkyl" denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl.

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl.

The term "cycloalkyl", as used herein alone or as part of another group, denotes optionally substituted, saturated cyclic hydrocarbon ring systems, including bridged ring systems, desirably containing 1 to 3 rings and 3 to 9 carbons per ring. Exemplary unsubstituted such groups include, but are not limited to, cyclopropyl, cyclobutyl, cyclopentyl, cyclohexyl, cycloheptyl, cyclooctyl, cyclodecyl, cyclododecyl, and adamantyl. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.",. 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The term "amino" denotes the radical —$NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. Illustrative examples include, but are not limited to, fluorene, 10,11-dihydro-5H-dibenzo[a,d]cycloheptene and 2,2a,7,7a-tetrahydro-1H-cyclobuta[a]indene.

The term "isotopic enrichment" refers to a process by which the relative abundance of an isotope of a given element are altered, thus producing a form of the element that has been enriched in one particular isotope and depleted in its other isotopic forms.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations. Compounds having hydrogens replaced by deuterium may form polymorphs which may enhance their solubility and/or bioavailability properties.

The term "deuterated analogs" as used herein alone or as part of a group, denote optionally substituted deuterium atoms in place of hydrogen.

Kushner and coworkers (Kushner, D. J.; Baker, A.; Dunstall, T. G. Can J. Physiol Pharmacol, 77(2), (1999) p. 79-88) have presented examples of how incorporating deuterium into a drug can often reduce the level of metabolic induced transformations especially those mediated by Cytochrome P450. This reduce rate of Cytochrome P450 induce metabolism can sometimes translate directly to enhanced bioavailablity. The reason for this is due to the fact that atomic substitution of a hydrogen by a deuterium in a drug alters the strength of the carbon-deuterium bond of the drug, while keeping it's 3D surface identical to the nondeuterated version. Substitution of deuterium for hydrogen, can give rise to an isotope effect that can alter the pharmacokinetics of the drug. In a reaction in which the cleavage of a C—H bond is rate determining the same reaction of the C-D analogue will be reduced. For example Schneider and coworkers (Scheneider, F.; et al., BiRDS Pharma GmbH, Arzneimittel Forschung (2006), 56(4), p. 295-300) have shown that replacing several of the hydrogen atoms around one of the aromatic rings of the COX-2 inhibitor Refecoxib (4-(4-methylsulfonylphenyl)-3-phenyl-5H-furan-2-one) with deuterium (at positions 2',3', 4',5' an 6') enhanced the oral bioavailability of the drug without affecting it's COX-2 selectivity.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences*, 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "N-oxide" denotes compounds that can be obtained in a known manner by reacting a compound of the present invention including a nitrogen atom (such as in a pyridyl group) with hydrogen peroxide or a peracid, such as 3-chloroperoxy-benzoic acid, in an inert solvent, such as dichloromethane, at a temperature between about −10-80° C., desirably about 0° C.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;
OC(S)NH—($C_1$-$C_4$ alkyl);
OC(S)N($C_1$-$C_4$ alkyl)$_2$;
SH;
S—($C_1$-$C_4$ alkyl);
S(O)—($C_1$-$C_4$ alkyl);
S(O)$_2$—($C_1$-$C_4$ alkyl);
SC(O)—($C_1$-$C_4$ alkyl);
SC(O)O—($C_1$-$C_4$ alkyl);
$NH_2$;
N(H)—($C_1$-$C_4$ alkyl);
N($C_1$-$C_4$ alkyl)$_2$;
N(H)C(O)—($C_1$-$C_4$ alkyl);
N($CH_3$)C(O)—($C_1$-$C_4$ alkyl);
N(H)C(O)—$CF_3$;
N($CH_3$)C(O)—$CF_3$;
N(H)C(S)—($C_1$-$C_4$ alkyl);
N($CH_3$)C(S)—($C_1$-$C_4$ alkyl);
N(H)S(O)$_2$—($C_1$-$C_4$ alkyl);
N(H)C(O)$NH_2$;
N(H)C(O)NH—($C_1$-$C_4$ alkyl);
N($CH_3$)C(O)NH—($C_1$-$C_4$ alkyl);
N(H)C(O)N($C_1$-$C_4$ alkyl)$_2$;
N($CH_3$)C(O)N($C_1$-$C_4$ alkyl)$_2$;
N(H)S(O)$_2$$NH_2$;
N(H)S(O)$_2$NH—($C_1$-$C_4$ alkyl);
N($CH_3$)S(O)$_2$NH—($C_1$-$C_4$ alkyl);
N(H)S(O)$_2$N($C_1$-$C_4$ alkyl)$_2$;
N($CH_3$)S(O)$_2$N($C_1$-$C_4$ alkyl)$_2$;
N(H)C(O)O—($C_1$-$C_4$ alkyl);
N($CH_3$)C(O)O—($C_1$-$C_4$ alkyl);
N(H)S(O)$_2$O—($C_1$-$C_4$ alkyl);
N($CH_3$)S(O)$_2$O—($C_1$-$C_4$ alkyl);
N($CH_3$)C(S)NH—($C_1$-$C_4$ alkyl);
N($CH_3$)C(S)N($C_1$-$C_4$ alkyl)$_2$;
N($CH_3$)C(S)O—($C_1$-$C_4$ alkyl);
N(H)C(S)$NH_2$;
$NO_2$;
$CO_2H$;
$CO_2$—($C_1$-$C_4$ alkyl);
C(O)N(H)OH;
C(O)N($CH_3$)OH:
C(O)N($CH_3$)OH;
C(O)N($CH_3$)O—($C_1$-$C_4$ alkyl);
C(O)N(H)—($C_1$-$C_4$ alkyl);
C(O)N($C_1$-$C_4$ alkyl)$_2$;
C(S)N(H)—($C_1$-$C_4$ alkyl);
C(S)N($C_1$-$C_4$ alkyl)$_2$;
C(NH)N(H)—($C_1$-$C_4$ alkyl);
C(NH)N($C_1$-$C_4$ alkyl)$_2$;
C($NCH_3$)N(H)—($C_1$-$C_4$ alkyl);
C($NCH_3$)N($C_1$-$C_4$ alkyl)$_2$;
C(O)—($C_1$-$C_4$ alkyl);
C(NH)—($C_1$-$C_4$ alkyl);
C($NCH_3$)—($C_1$-$C_4$ alkyl);
C(NOH)—($C_1$-$C_4$ alkyl);
C($NOCH_3$)—($C_1$-$C_4$ alkyl);
CN;
CHO;
$CH_2OH$;
$CH_2O$—($C_1$-$C_4$ alkyl);
$CH_2NH_2$;
$CH_2N$(H)—($C_1$-$C_4$ alkyl);
$CH_2N$($C_1$-$C_4$ alkyl)$_2$;
aryl;
heteroaryl;
cycloalkyl; and
heterocyclyl.

In one embodiment of the present invention, the matalloprotease inhibiting compounds may be represented by the general Formula (I-XIII):

(I-XIII)

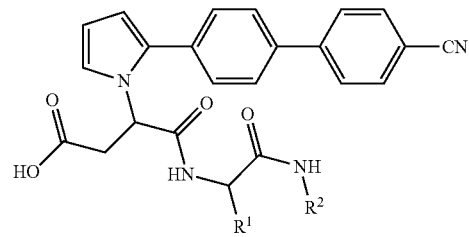

I

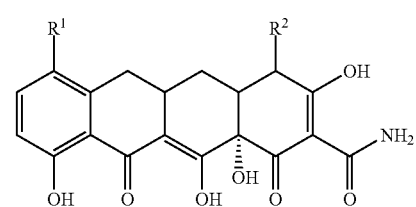

II

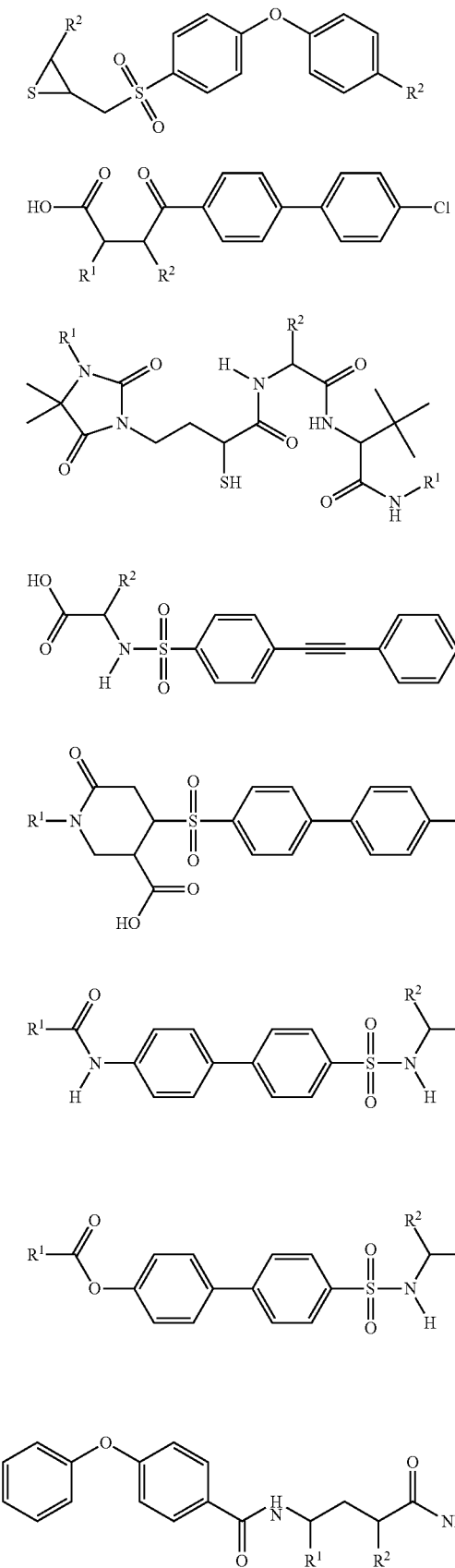

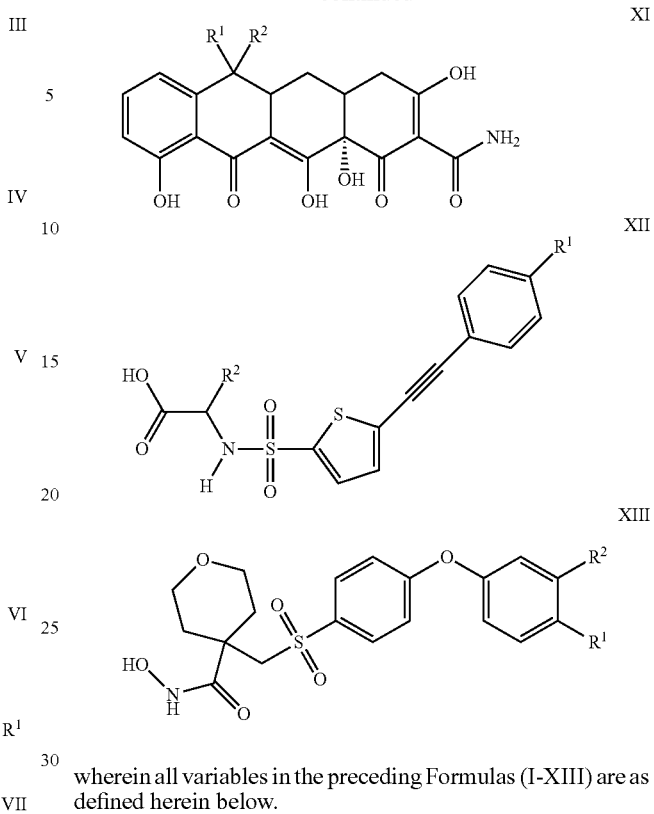

wherein all variables in the preceding Formulas (I-XIII) are as defined herein below.

$R^1$, $R^2$ is independently selected from the group consisting of hydrogen, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, hydroxy, alkoxy, aryl, heteroaryl, arylalkyl, heteroarylalkyl, alkenyl, alkynyl, $NO_2$, $NR^9R^9$, $NR^9NR^9R^9$, $NR^9N=CR^9R^9$, $NR^9SO_2R^9$, CN, $C(O)OR^9$, and fluoroalkyl, wherein alkyl, cycloalkyl, alkoxy, alkenyl, alkynyl and fluoroalkyl are optionally substituted one or more times and heterocycloalkyl fused heteroarylalkyl are optionally substituted one or more times;

N-oxides, deuterated analogs, pharmaceutically acceptable salts, prodrugs, formulations, tautomers, racemic mixtures or stereoisomers thereof.

It is contemplated that the compounds of the present invention represented by the Formulas described above include all diastereomers and enantiomers, as well as racemic mixtures. Racemic mixtures may be separated by chiral salt resolution or by chiral column HPLC chromatography. As was motioned above the compounds of the present invention represented by the Formulas described above include deuterated analogs in which one or more hydrogens of the molecule are replaced by deuterium atoms.

More specifically, the compounds of Formula (I-XIII) may be selected from, but are not limited to, the following:
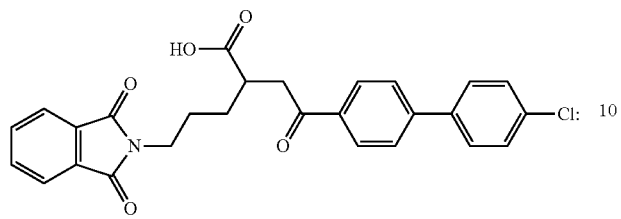
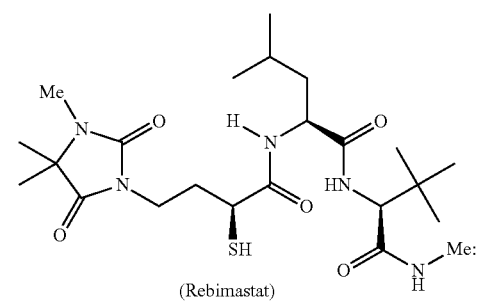
(Rebimastat)
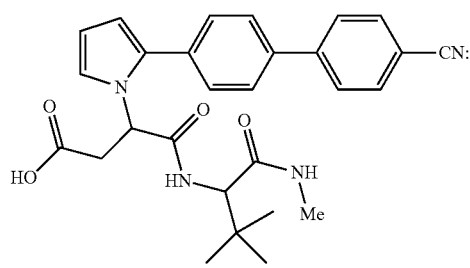
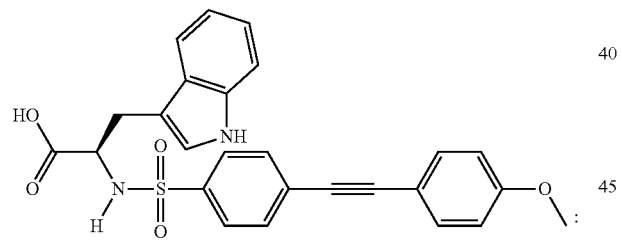
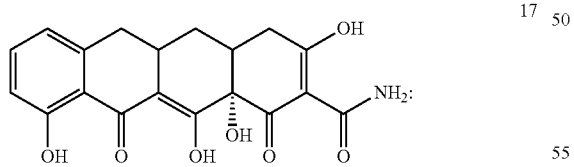
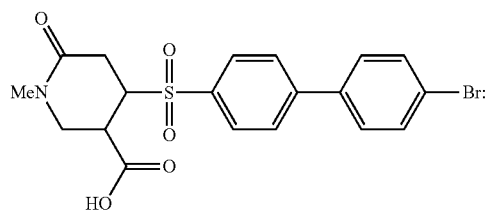
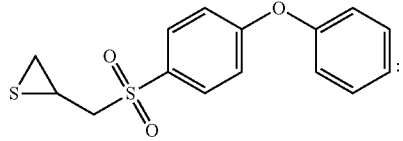
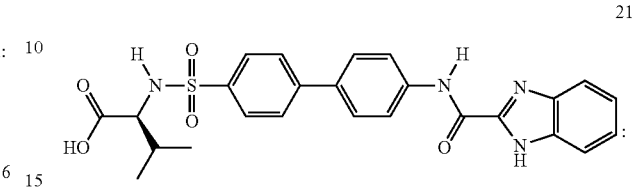
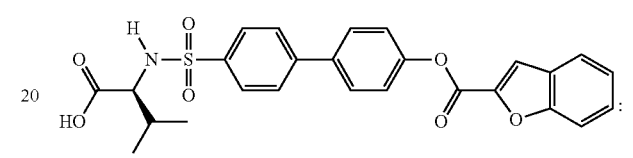
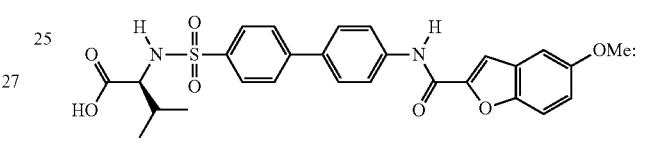
(Tanomastat)
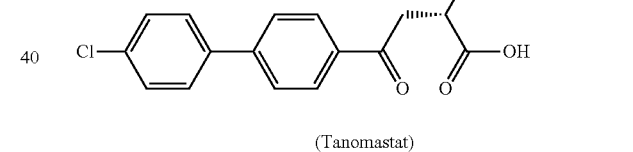
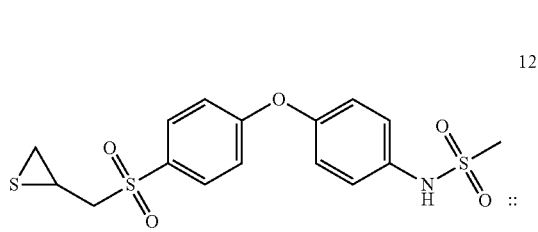
(ONO 4817)

-continued
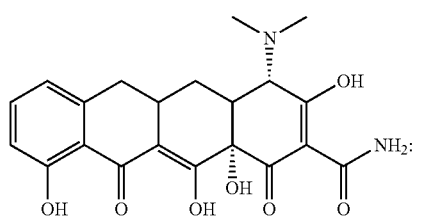
(Sancycline)
5 (S3304)
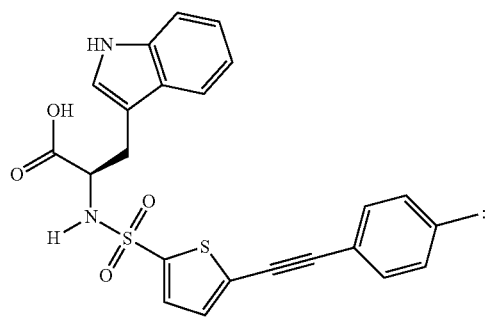
10
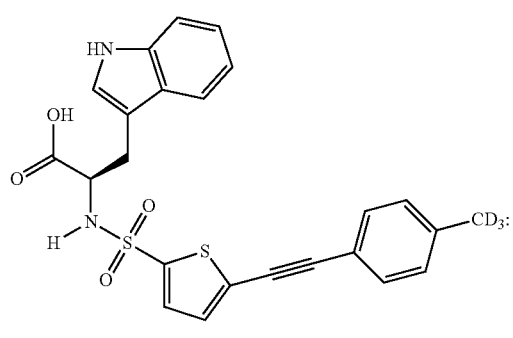
14
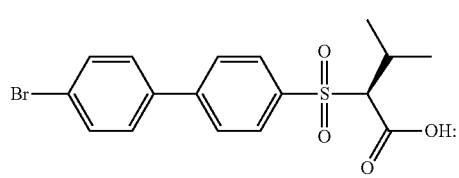
(PD 166793)
18
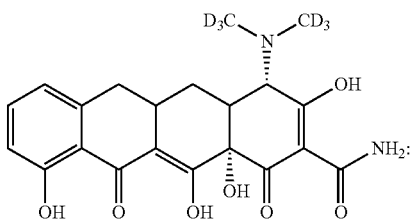
17
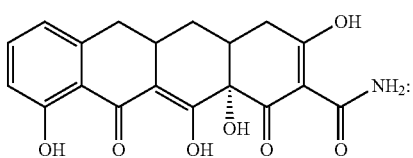
-continued
23
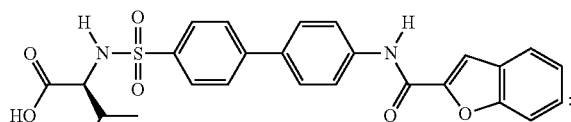
38
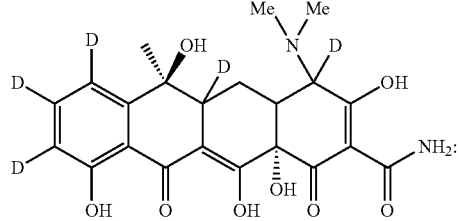
39
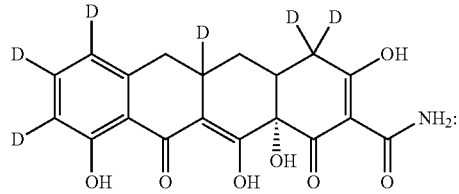
37
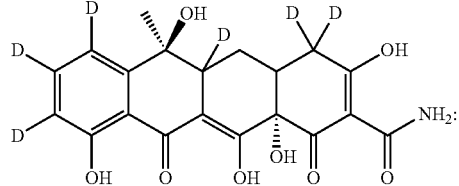
34
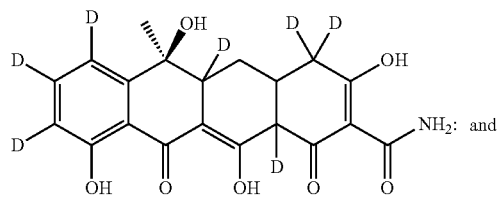
and
40
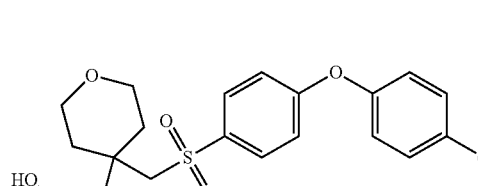
(RO113-0830)
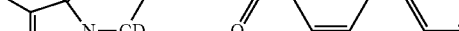

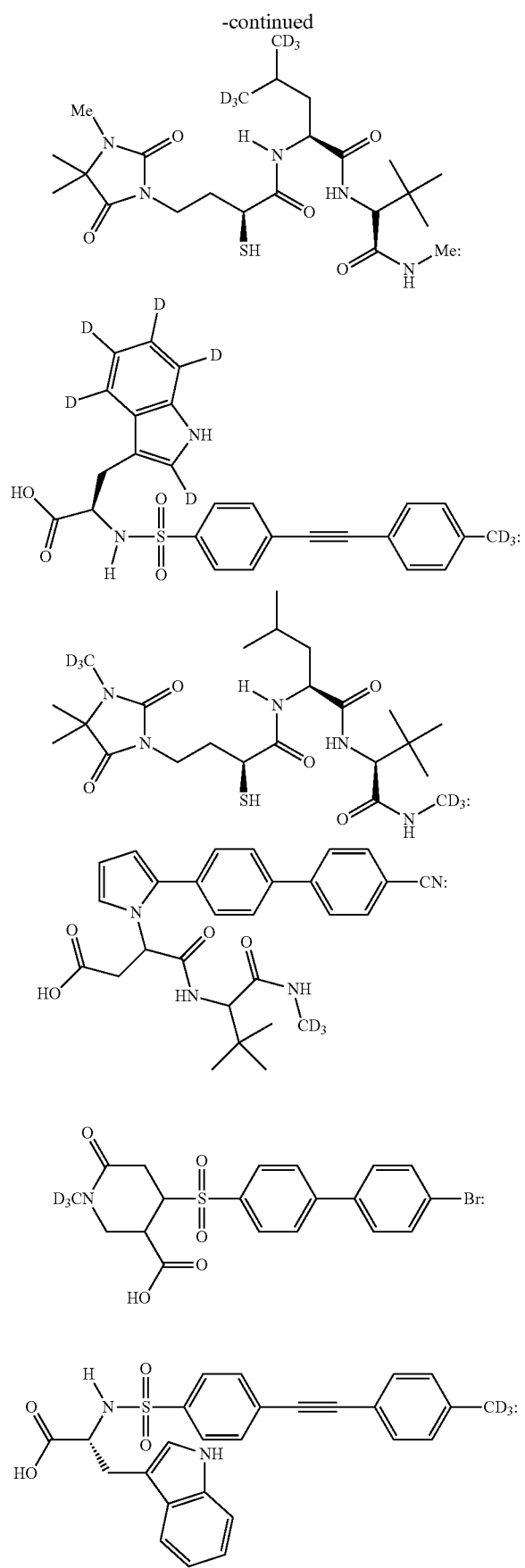
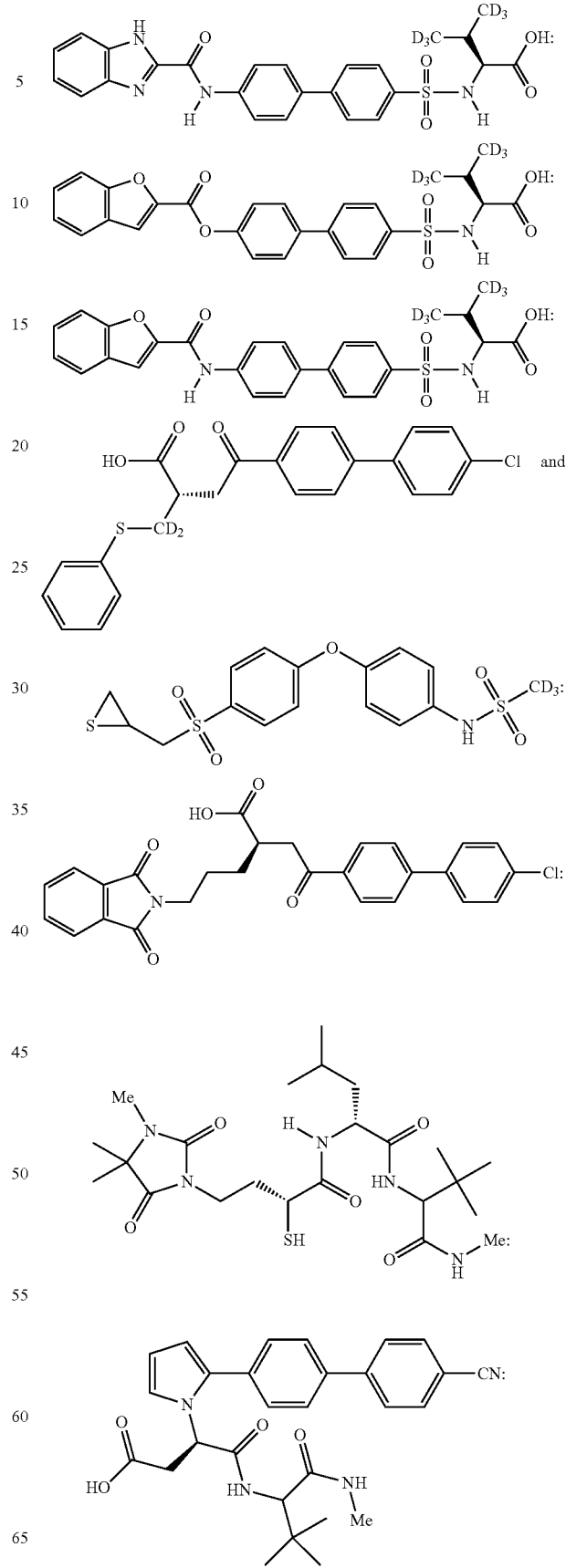

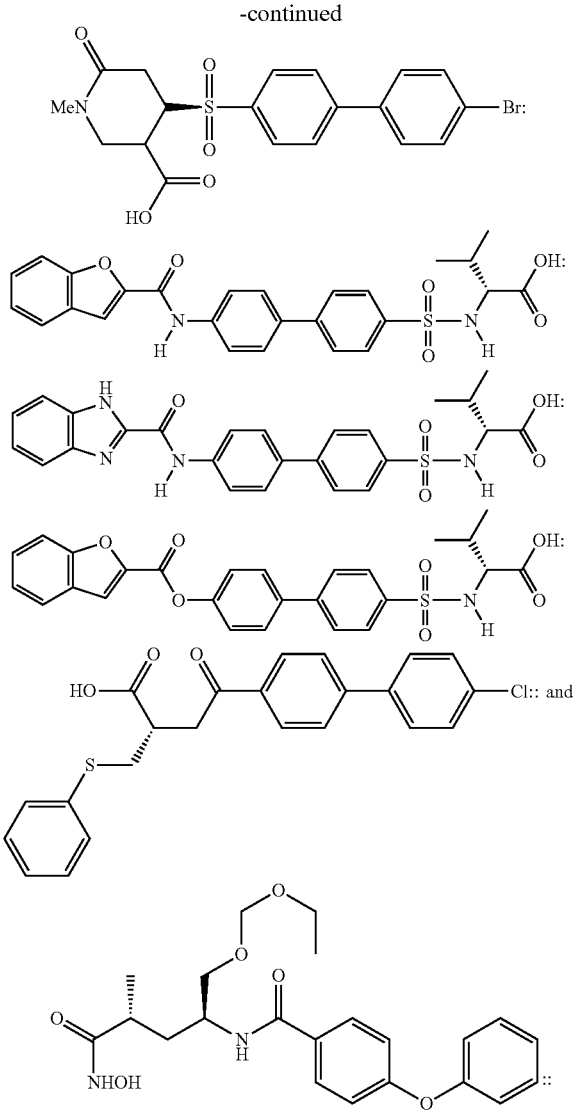

The present invention also is directed to pharmaceutical compositions including any of the MMP-2 and/or MMP-9 inhibiting compounds of the present invention described above. In accordance therewith, some embodiments of the present invention provide a pharmaceutical composition which may include an effective amount of a MMP-2 and/or MMP-9 inhibiting compound of the present invention and a pharmaceutically acceptable carrier.

The present invention also is directed to methods of inhibiting MMP-2 and/or MMP-9 and methods of treating diseases or symptoms mediated by an MMP-2 and/or MMP-9 enzyme. Such methods include administering a MMP-2 and/or MMP-9 inhibiting compound of the present invention, such as a compound of Formula (I-XIII), as defined above, deuterated analog or an N-oxide, pharmaceutically acceptable salt, polymorph or stereoisomer thereof. Examples of diseases or symptoms mediated by an MMP-2 and/or MMP-9 enzyme include, but are not limited to exaggerated sensitivity to pain, such as hyperalgesia, causalgia and allodynia; acute pain; burn pain; mechanically induced pain; atypical facial pain; neuropathic pain; back pain; complex regional pain syndromes I and II; arthritic joint pain; sports injury pain; pain related to viral infection, and post-herpetic neuralgia; phantom limb pain; labor pain; cancer pain; post-chemotherapy pain; post-stroke pain; post-operative pain; physiological pain; inflammatory pain; acute inflammatory conditions/visceral pain, angina, irritable bowel syndrome (IBS), and inflammatory bowel disease; neuropathic pain; neuralgia; painful diabetic neuropathy; traumatic nerve injury; spinal cord injury; and tolerance to opioids or withdrawal from opioids or other narcotics.

In some embodiments of the present invention, the MMP-2 and/or MMP-9 inhibiting compounds defined above are used in the manufacture of a medicament for the treatment of a disease mediated by an MMP-2 and/or MMP-9.

In some embodiments, the MMP-2 inhibiting compounds defined above may be used in combination with a drug, agent or therapeutic such as, but not limited to: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) an opioid or (i) other anti-inflammatory agents or therapeutics useful for the treatment of chemokine mediated diseases.

Examples of disease modifying antirheumatic drugs include, but are not limited to, methotrexate, azathioptrineluflunomide, penicillamine, gold salts, mycophenolate, mofetil and cyclophosphamide.

Examples of nonsteroidal anti-inflammatory drugs include, but are not limited to, piroxicam, ketoprofen, naproxen, indomethacin, and ibuprofen.

Examples of COX-2 selective inhibitors include, but are not limited to, rofecoxib, celecoxib, and valdecoxib.

An example of a COX-1 inhibitor includes, but is not limited to, piroxicam.

Examples of immunosuppressives include, but are not limited to, methotrexate, cyclosporin, leflunimide, tacrolimus, rapamycin and sulfasalazine.

Examples of steroids include, but are not limited to, p-methasone, prednisone, cortisone, prednisolone and dexamethasone.

Examples of biological response modifiers include, but are not limited to, anti-TNF antibodies, TNF-α antagonists, IL-1 antagonists, anti-CD40, anti-CD28, IL-10 and anti-adhesion molecules.

Examples of anti-inflammatory agents or therapeutics include, but are not limited to, p38 kinase inhibitors, PDE4 inhibitors, TACE inhibitors, chemokine receptor antagonists, thalidomide, leukotriene inhibitors and other small molecule inhibitors of pro-inflammatory cytokine production.

In accordance with another embodiment of the present invention, a pharmaceutical composition may include an effective amount of a compound of the present invention, a pharmaceutically acceptable carrier and a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) an opioid; or (h) other anti-inflammatory agents or therapeutics useful for the treatment of chemokine mediated diseases.

The MMP inhibiting activity of the MMP inhibiting compounds of the present invention may be measured using any suitable assay known in the art. A standard in vitro assay for MMP-2 inhibiting activity is described in Example 130 and for MMP-9 is described in Example 131. Additionally, standard in vitro assays for measuring MMP-1, MMP-7, MMP-3, MMP-12 and MMP-13 are described in Examples 132-136. Standard in vitro assays for measuring human and mouse microsomal stability is presented in Example 105. The in vivo pain inhibiting properties of the MMP inhibiting compounds of the present invention may be measured using any suitable animal model known in the art. A standard in vivo test for measuring neuropathic pain inhibition is described in Examples 110 and 111 and a test for measuring inflammatory pain is described in Example 120. Finally, a standard in vivo test for measuring morphine tolerance and naloxone-precipitated morphine withdrawal is described in Example 125.

The MMP inhibiting compounds of the invention may have an inhibition activity ($IC_{50}$ MMP-2 and/or MMP-9) ranging from about 0.2 nM to about 20 µM, and typically, from about 1 nM to about 2 µM. The synthesis of MMP inhibiting compounds of the present invention and their biological assay are described in the following examples which are not intended to be limiting in any way.

EXAMPLES AND METHODS

All reagents and solvents would be obtained from commercial sources and used without further purification. Proton ($^1$H) spectra would be recorded on a NMR spectrometer in deuterated solvents. Flash chromatography would be performed using Merck silica gel, grade 60, 70-230 mesh using suitable organic solvents as indicated in specific examples. Thin layer chromatography (TLC) would be carried out on silica gel plates with UV detection.

Example 1

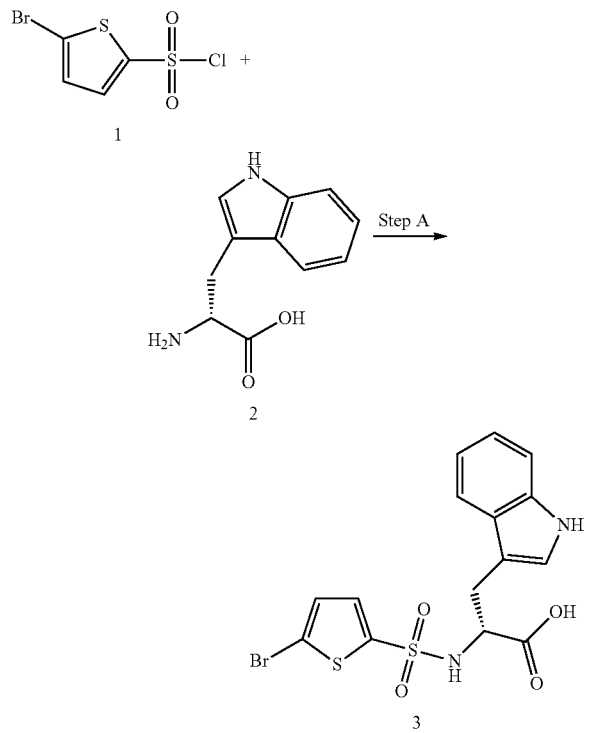

Step A

To a suspension of (R)-2-Amino-3-(1H-indol-3-yl)-propionic acid 2 (0.23 g, 1.12 mmol) (Alfa-Aesar, A-18426) in acetone (3 mL) was added 2M sodium carbonate (1 mL) to stir at room temperature for 30 minutes. To this mixture was added bromosulfonyl chloride 1 (0.13 g, 0.5 mmol) (Alfa-Aesar, A-14677) at 0° C. to stir for 15 minutes. The reaction mixture was stirred further for 1 hour at room temperature. After pouring into water (20 mL), the solution was washed with ether (×3). The aqueous layer was acidified with 1M HCl, followed by extraction with ethyl acetate (×3). The combined organic extracts were then washed with brine and dried ($Na_2SO_4$) to provide the crude (R)-2-(5-Bromo-thiophene-2-sulfonylamino)-3-(1H-indol-3-yl)-propionic acid product (3) (0.16 g, 74%). LC-MS (ES+) 429, 431; (ES−) 427, 429.

A portion of the crude (R)-2-(5-Bromo-thiophene-2-sulfonylamino)-3-(1H-indol-3-yl)-propionic acid product (3) was taken to the next step without further purification.

Example 2

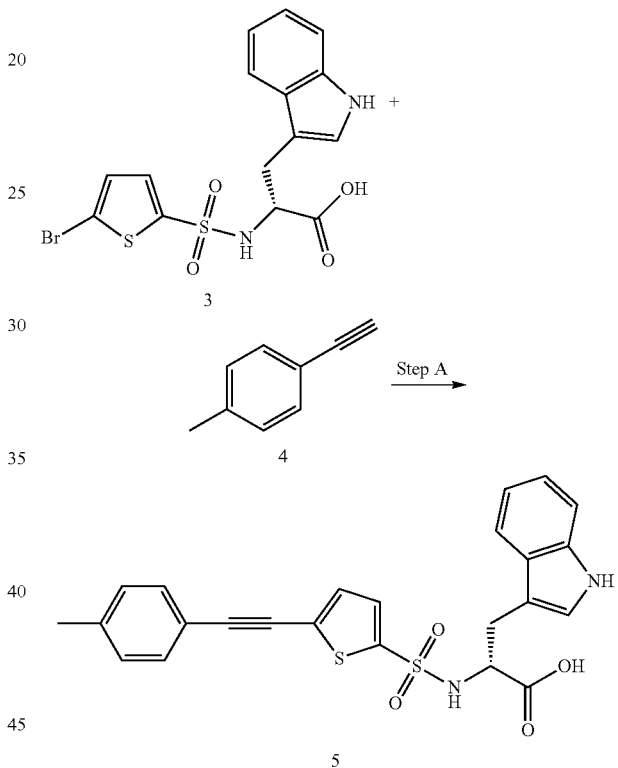

Step A

In a round bottom flask was added crude (R)-2-(5-Bromo-thiophene-2-sulfonylamino)-3-(1H-indol-3-yl)-propionic acid (3) (60 mg, 0.14 mmol), p-tolyl acetylene 4 (480 mg, 0.41 mmol), $PdCl_2P(PPh_3)_2$ (10 mg, 0.015 mmol), copper(I) iodide (2 mg, 0.01 mmol) and triethylamine (0.025 g, 0.25 mmol) and then dissolved in dry DMF (2 mL) under an atmosphere of nitrogen. The reaction mixture was then heated at 50° C. under a nitrogen atmosphere for 2 hours. The reaction mixture was then cooled to room temperature and diluted with ethyl acetate and washed with a solution composed of NaCl/$NaHCO_3$/$(NH_4)_2CO_3$/water (1:1:1:1) (×3), water, and then dried over sodium sulfate ($Na_2SO_4$). The crude product was purified using a SAX column to provide to give the desired (R)-3-(1H-Indol-3-yl)-2-(5-p-tolylethynyl-thiophene-2-sulfonylamino)-propionic acid 5 (0.036 g, 55%).

Example 2, Reaction A was repeated with same scale as above and then combined with the previous batch. The combined products were then further purified using preparative, reversed-phase-HPLC to give (R)-3-(1H-Indol-3-yl)-2-(5-p-tolylethynyl-thiophene-2-sulfonylamino)-propionic acid 5 having a purity of >95% by HPLC. LC-MS (ES+) 465; (ES−) 463; $^1$H NMR (300 MHz, DMSO-d6) δ 2.35 (s, 3H), 2.86-2.94 (m, 1H), 3.08-3.16 (m, 1H), 3.96-4.40 (m, 1H), 6.93-7.50 (m, 11H), 8.67 (d, 1H, J=8.7 Hz), 10.83 (s, 1H).

Example 3

Synthesis of 4-Iodotoluine (D3, 98%) Starting Material

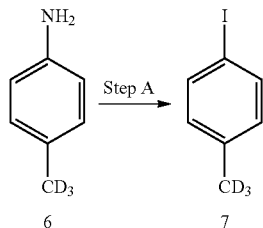 [SMILES: [2H]C([2H])([2H])c1ccc(N)cc1 ; [2H]C([2H])([2H])c1ccc(I)cc1]

Step A

Following the classic method of Griess (Practical Organic Chemistry, Richard Clay & Sons, page 144, Preparation #60, (1900)) in which 0.2 grams (1.8 mmoles) of toluidine (D3, 98%), commercially obtained from C/D/N Isotopes (Quebec, Canada) (6) is combined with 0.4 ml $D_2SO_4$ (obtained commercially from Cambridge Isotope Laboratories, Andover, Mass.) and the resulting mixture cooled until the temperature of the stirred mixture reaches 0° C. and then 160 mg (2.32 mmole) of sodium nitrite was slowly added in three portions over 10 minutes making sure that the temperature does not rise above 10° C. After the sodium nitrite has been added, a solution composed of 48 mg (2.9 mmole) of KI in 1 ml $D_2O$ (obtained commercially from Cambridge Isotope Laboratories) was then added and the reaction mixture was allowed to warm to room temperature and stirred for 1 hour. The reaction mixture was then diluted with $D_2O$ (10 mL) and extracted with ether (×2). The ether layer was then washed with 10% $Na_2S_2O_3$ in $D_2O$ (×2) and dried over anhydrous sodium sulphate. The crude product (7) was then purified by column chromatography using hexane as the eluent to obtain the desired pure 4-Iodotoluene (D3, 98%) product (7) (0.16 g, 40%). $^1$H NMR (300 MHz, CDCl$_3$): δ, 6.93 (d, 2H, J=7.8 Hz), 7.56 (d, 2H, J=7.8 Hz).

When the $D_2SO_4$ was replaced by DCl (obtained commercially from Cambridge Isotope Laboratories, Andover, Mass.) only a 20% yield of 7 was obtained.

Example 4

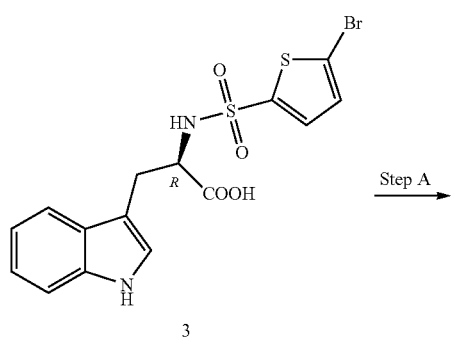

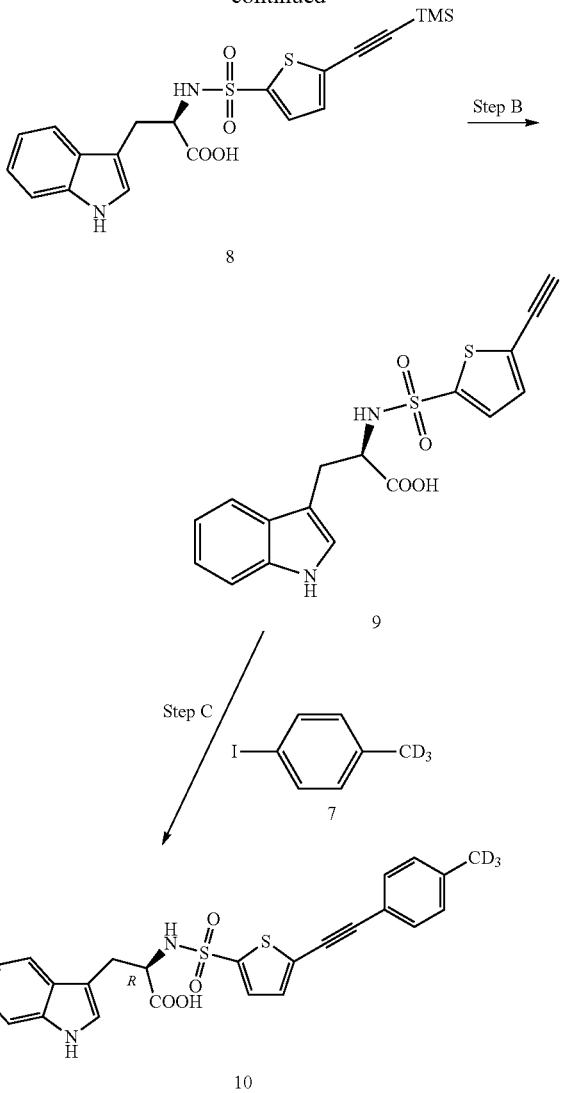

Step A

In a round bottom flask was added crude compound (R)-2-(5-Bromo-thiophene-2-sulfonylamino)-3-(1H-indol-3-yl)-propionic acid product (3) (0.25 g, 0.584 mmol) (synthesized via Example 1, Step A), commercially available ethynyltrimethylsilane (0.17 g, 1.73 mmol), PdCl$_2$P(PPh$_3$)$_2$ (0.041 g, 0.061 mmol), copper(I)iodide (0.006 g, 0.0315 mmol), and triethylamine (0.177 g, 1.75 mmol) dissolved in dry DMF (3 mL) under an atmosphere of nitrogen and mixture heated at 50° C. for two hours. The reaction mixture was then diluted with ethyl acetate and washed with a solution composed of NaCl/NaHCO$_3$/(NH$_4$)$_2$CO$_3$/water (1:1:1:1) (×3), water, brine, and dried (Na$_2$SO$_4$) to give the desired crude (R)-3-(1H-Indol-3-yl)-2-(5-trimethylsilanyl-ethynyl-thiophene-2-sulfonylamino)-propionic acid 8 (185 mg, 71%). LC-MS (ES+) 447; (ES−) 445.

Step B

To a solution of crude (R)-3-(1H-Indol-3-yl)-2-(5-trimethylsilanylethynyl-thiophene-2-sulfonylamino)-propionic acid 8 (0.126 g, 0.282 mmol) in dichloromethane/methanol mixture (1:1, 10 mL) was added K$_2$CO$_3$ (0.047 g, 0.34 mmol) and allowed to stir for 60 minutes. The reaction mixture was then filtered and retentate washed with dichloromethane-methanol mixture. The combined filtrate was concentrated under reduced pressure and then purified using a SAX column to obtain (R)-2-(5-Ethynyl-thiophene-2-sulfonylamino)-3-(1H-indol-3-yl)-propionic acid 9 (52 mg, 49%). LC-MS (ES+) 375; (ES−) 373.

Step C

In a round bottom flask was added (R)-2-(5-Ethynyl-thiophene-2-sulfonylamino)-3-(1H-indol-3-yl)-propionic acid 9 (0.052 g, 0.139 mmol), iodotoluene-(D3, 98%) 7 (0.061 g, 0.28 mmol) (obtained from commercially available 4-aminotoluene (D3, 98%) via Sandmeyer reaction outlined in Example 3), $PdCl_2P[(PPh_3)]_2$ (0.01 g, 0.015 mmol), copper (I)iodide (0.002 g, 0.0105 mmol) and triethylamine (0.025 g, 0.247 mmol) and dissolved in dry DMF (3 mL) under an atmosphere of nitrogen and mixture heated at 50° C. for 2 hours. The reaction mixture was cooled, diluted with ethyl acetate and washed with a solution composed of NaCl/ $NaHCO_3/(NH_4)_2CO_3$/water (1:1:1:1) (×3), water, brine, and then dried over sodium sulfate ($Na_2SO_4$). The mixture was filtered and the filtrate was evaporated under reduced pressure to give crude 10 which was purified via SAX Column chromatography to give purified 10 (0.025 g, 38%). The product was further purified by preparative, reversed-phase-HPLC to obtain the desired product 10 (R)-3-(1H-Indol-3-yl)-2-[5-(4-trideuteromethyl-phenylethynyl)-thiophene-2-sulfonylamino]-propionic acid-(D3, 98%) in >95% purity by HPLC. LC-MS (ES+) 468; (ES−) 466.

$^1$H NMR (300 MHz, MeOH-d4) δ 3.17-3.25 (m), 4.32-4.35 (m), 5.60-5.66 (m), 7.05-7.68 (m), 10.4 (br s).

Example 5

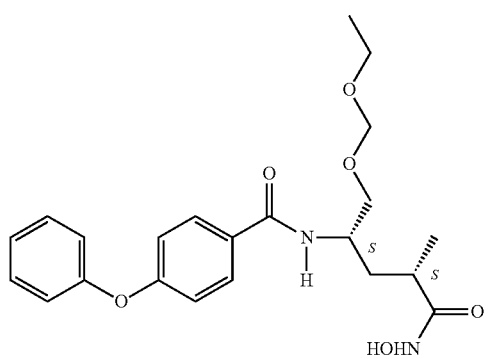

N-(1-Ethoxymethoxymethyl-3-hydroxycarbamoyl-butyl)-4-phenoxy-benzamide (11) (ONO 4817) can be obtained commercially from Tocris Biosciences (Ellisville, Mo.).

Example 6

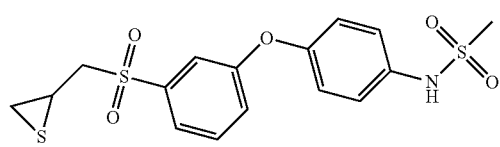

N-[4-(3-Thiiranylmethanesulfonyl-phenoxy)-phenyl]-methanesulfonamide (12) (Lipton et al. WO2006/036928 and Ike-jiri, M. et al. Journal of Biological Chem., 280, 33992, (2005)) can be commercially obtained from EMD Biosciences, Inc. (Gibbstown, N.J.).

Example 7

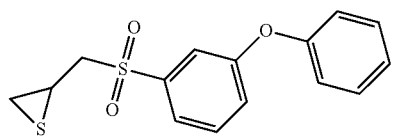

2-(3-Phenoxy-benzenesulfonylmethyl)-thiirane (13) (Lipton et al. WO2006/036928 and Kleifeld, O. et al. Journal of Biological Chem., 276, 17126, (2001)) can be commercially obtained from EMD Biosciences, Inc. (Gibbstown, N.J.) or from Biomol (Pymouth Meeting, Pa.).

Example 8

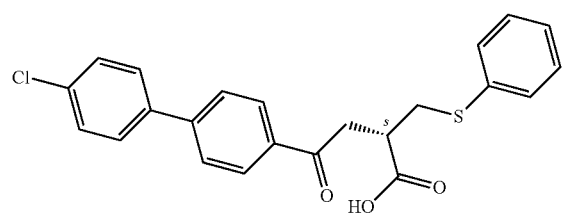

4-(4'-Chloro-biphenyl-4-yl)-4-oxo-2-phenylsulfanylmethyl-butyric acid (14) [Tanomastat] can be commercially obtained from Toronto Research Chemicals, Inc. (Ontario, Canada) or from Texas Biochemicals, Inc. (College Station, Tex.) or can be synthesized via literature procedure ((Kluender H. et al. U.S. Pat. No. 5,886,022 (1999)).

Example 9

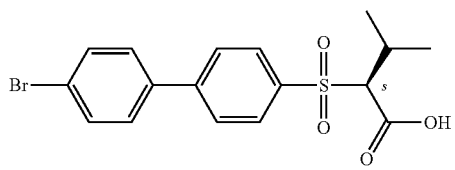

2-(4'-Bromo-biphenyl-4-sulfonyl)-3-methyl-butyric acid (15) [PD 166793]] can be commercially obtained from Tocris Biosciences (Ellisville, Mo.).

Example 10

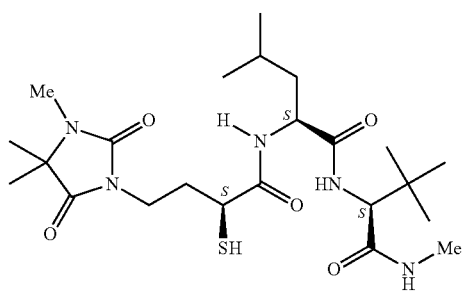

2-[2-Mercapto-4-(3,4,4-trimethyl-2,5-dioxo-imidazolidin-1-yl)-butyrylamino]-4-methyl-pentanoic acid (2,2-dimethyl-1-methylcarbamoyl-propyl)-amide (16) [Rebimastat or BMS-275299] (France, S.; Organic Letters, 2005 (7(14), 3009, (2005)) can be commercially obtained from Finechemie & Pharma Co., Ltd. (Chongquing, China) or China CSPC Pharmaceutical Group (Shijiazhuang, China) or synthesized via the cited literature procedure (France, S.; Organic Letters, 2005 (7(14), 3009, (2005)).

Example 11

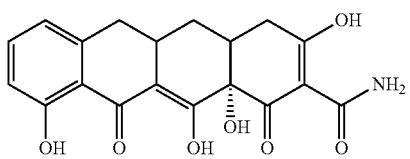

3,10,12,12a-Tetrahydroxy-1,11-dioxo-1,4,4a,5,5a,6,11,12a-octahydro-naphthacene-2-carboxylic acid amide (17) (Rudek, M.; et al. J. Clinical Oncology, 19, 584-592 (2001)) can be obtained from Sigma-Aldrich (Milwaukee, Wis.).

Example 12

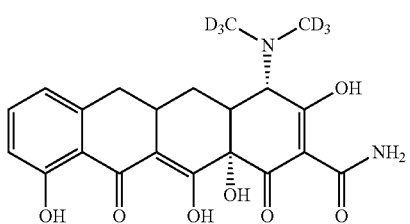

4-Dimethyl (D6, 98%) amino-3,10,12,12a-tetrahydroxy-1,11-dioxo-1,4,4a,5,5a,6,11,12a-octahydro-naphthacene-2-carboxylic acid amide (18) can be obtained from Toronto Research Chemicals, Inc. (Ontario, Canada).

Example 13

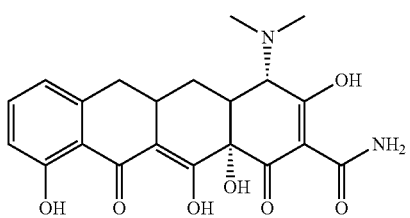

4-Dimethylamino-3,10,12,12a-tetrahydroxy-1,11-dioxo-1,4,4a,5,5a,6,11,12a-octahydro-naphthacene-2-carboxylic acid amide (19) (Sancycline) can be obtained from Toronto Research Chemicals, Inc. (Ontario, Canada).

Example 14

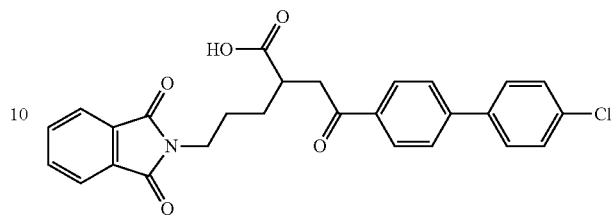

2-[2-(4'-Chloro-biphenyl-4-yl)-2-oxo-ethyl]-5-(1,3-dioxo-1,3-dihydro-isoindol-2-yl)-pentanoic acid (20) can be synthesized via literature procedures (Kluender H. et al. U.S. Pat. No. 5,886,022 (1999); Example 189).

Example 15

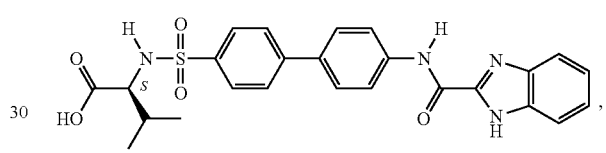

2-{4'-[(1H-Benzoimidazole-2-carbonyl)-amino]-biphenyl-4-sulfonylamino}-3-methyl-butyric acid (21) can be synthesized via literature procedures (Levin, J. I. et al. U.S. Pat. No. 7,420,001 B2 (2008)).

Example 16

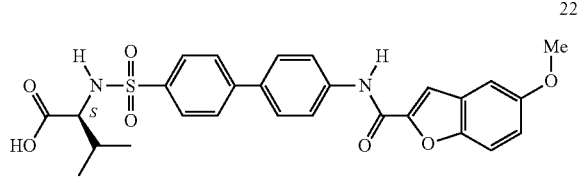

2-{4'-[(5-Methoxy-benzofuran-2-carbonyl)-amino]-biphenyl-4-sulfonylamino}-3-methyl-butyric acid (22) can be synthesized via literature procedures (Levin, J. I. et al. U.S. Pat. No. 7,420,001 B2 (2008)).

Example 17

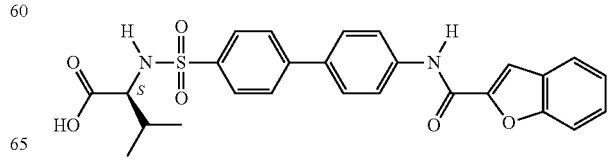

2-{4'-[(Benzofuran-2-carbonyl)-amino]-biphenyl-4-sulfonylamino}-3-methyl-butyric acid (23) can be synthesized via literature procedures (Levin, J. I. et al. U.S. Pat. No. 7,420,001 B2 (2008)).

Example 18

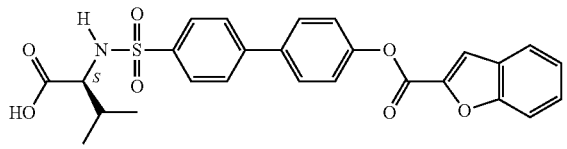

Benzofuran-2-carboxylic acid 4'-(1-carboxy-2-methyl-propylsulfamoyl)-biphenyl-4-yl ester (24) can be synthesized via literature procedures (Levin, J. I. et al. U.S. Pat. No. 7,420,001 B2 (2008)).

Example 19

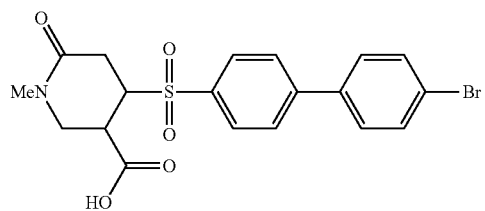

4-(4'-Bromo-biphenyl-4-sulfonyl)-1-methyl-6-oxo-piperidine-3-carboxylic acid (25) can be synthesized via literature procedures (Chung, Y. J.; et al. Bull. Korean Chem. Soc., 29(6), 1103-1104 (2008)).

Example 20

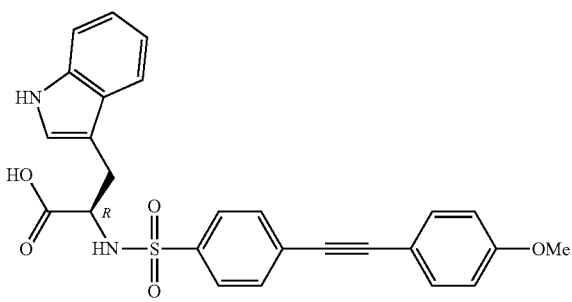

3-(1H-Indol-3-yl)-2-[4-(4-methoxy-phenylethynyl)-benzenesulfonylamino]-propionic acid (26) can be synthesized via literature procedures (Tamura, Y.; et al. J. Med. Chem. 41, 640-649, (1998)).

Example 21

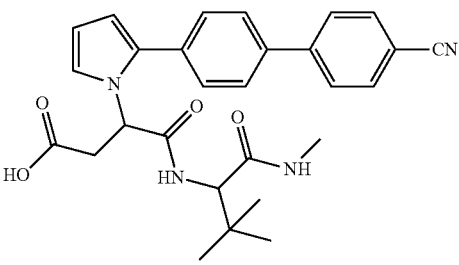

3-[2-(4'-Cyano-biphenyl-4-yl)-pyrrol-1-yl]-N-(2,2-dimethyl-1-methylcarbamoyl-propyl)-succinamic acid (27) can be synthesized via literature procedures (Whittaker, M.; et al. Chem. Rev. 99, 2735-2776 (1999) and references within).

Example 22

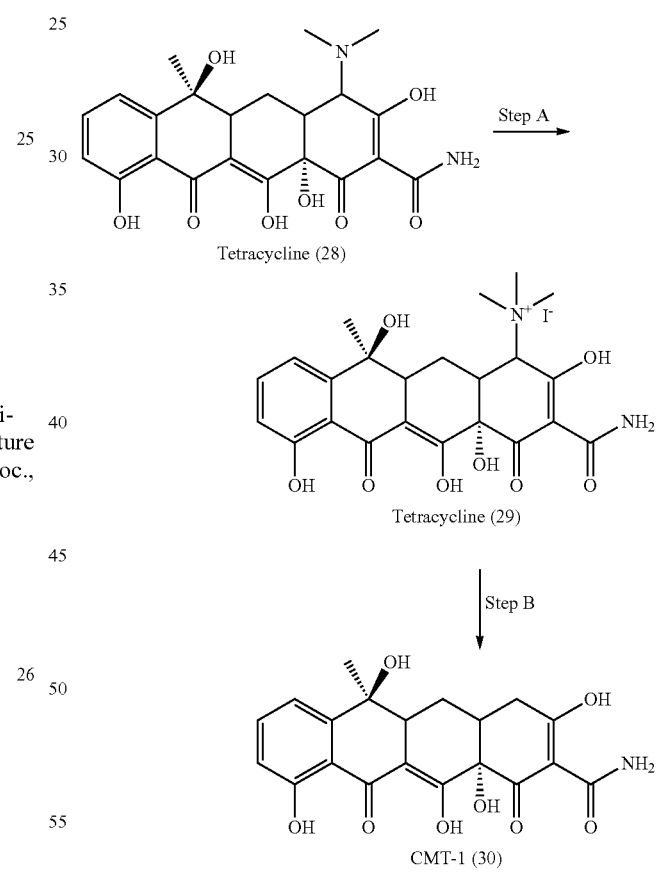

Step A
Golub and coworker (Golub, L. M.; et al., Journal of Dental Research, 66(8), 1310-1314, 1987) have found that the chemical removal of the N,N-dimethylamine group of tetracycline removes all antibacterial activity from the molecule. If one started with commercially obtained (Sigma-Aldrich, Milwaukee, Wis.) tetracycline (28) and then if methyl iodide is added and allowed to react it would then form the resulting trialkyl iodide intermediate (29).

Step B

The intermediate 29 could then be treated with zinc and acetic acid in water to give the resulting chemically modified tetracycline (CMT)-1 (30).

Example 23

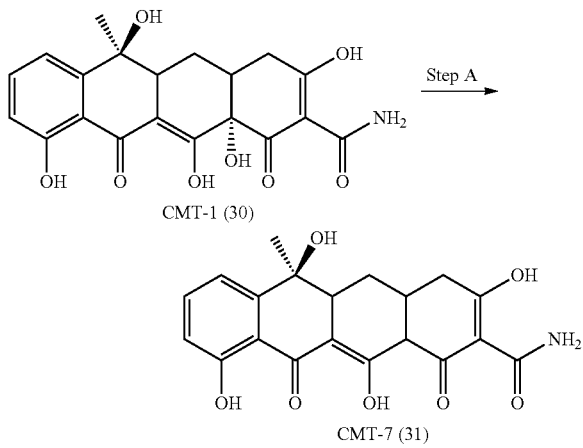

CMT-1 (30)

CMT-7 (31)

Step A

If one were to follow the method of Green and Booth (Green, A.; Booth, J. H.; Journal of the American Chemical Society, 82(15), 3950-3953, 1960), the dedimethyl tetracycline analog CMT-1 (30) can then undergo reductive elimination of the 12α-hydroxyl moiety with zinc and ammonium hydroxide in water to give the resulting chemically modified tetracycline (CMT)-7 (31).

Example 24

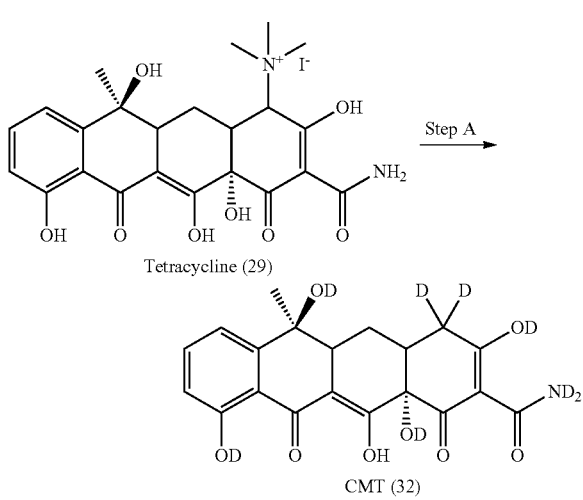

Tetracycline (29)

CMT (32)

↓ Step B

CMT (33)

Step A

In addition to removing the trialkyl ammonium group, the method of Golub and coworker (Golub, L. M.; et al., Journal of Dental Research, 66(8), 1310-1314, 1987) can also be used to incorporate deuterium in a regioselective manner, at the $C_4$-position of the "A" ring of the tetracycline molecule. The trialkyl iodide intermediate (29) can be treated with zinc and deuterated acetic acid in $D_2O$ to give the resulting dedimethylamine, deuterated tetracycline analog 32.

Step B

If one were to follow the method of Green and Booth (Green, A.; Booth, J. H.; Journal of the American Chemical Society, 82(15), 3950-3953, 1960), except that deuterated solvents can be used, the dedimethyl tetracycline analog 32 can undergo reductive elimination of the 12α-hydroxyl moiety with zinc and deuterated ammonium hydroxide in $D_2O$ to give the resulting deuterated CMT (33).

Example 25

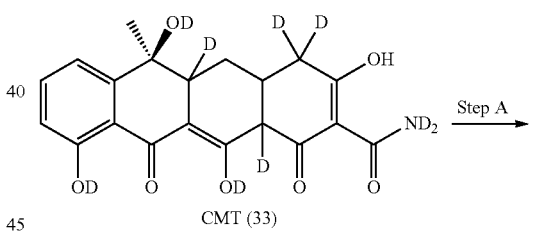

CMT (33)

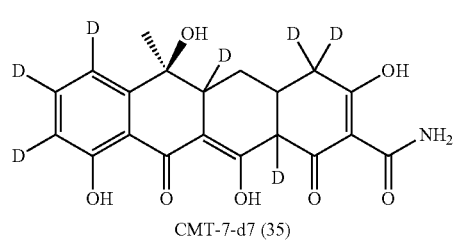

CMT-7-d7 (35)

Step A

If one were to use the work of Sajiki and coworkers (Sajiki, H.; et al. Synthetic Letters, No. 9, 1385-1388, 2005) CMT (33) can be treated with Palladium on carbon in the presence of hydrogen and deuterated water to give the resulting CMT- 7-d13 which can then be treated with H₂O to back exchange the amide and hydroxyl hydrogens to give the desired CMT-7-d7 (35).

Example 26

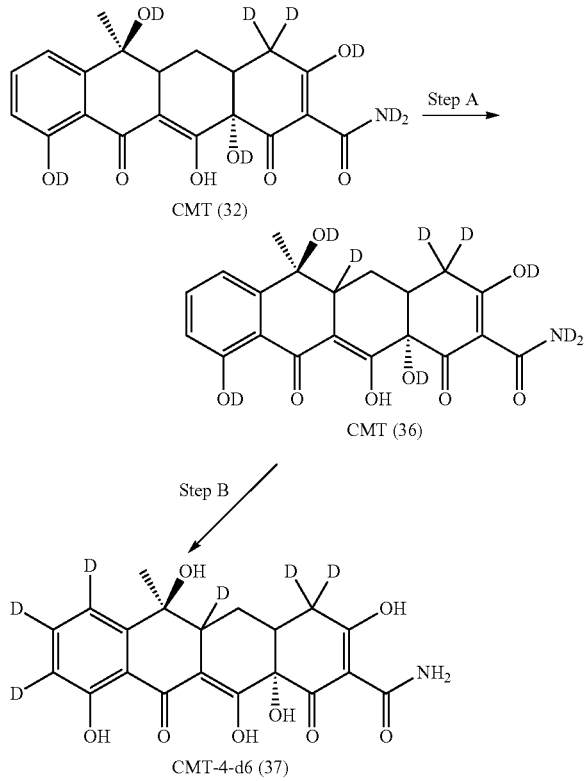

Step A

If one were to following the method of Yoshida and coworkers (Yoshida, T.; et al. Journal of the American Chemical Society, 101(8), 2027-2038, 1979), CMT-d8 (32) can be treated with palladium tris-triethylphosphine in deuterated water to give the resulting deuterated CMT (36).

Step B

CMT (36) can then be treated with Palladium on carbon in the presence of hydrogen and deuterated water to give the resulting CMT-4-d13 which will can then be treated with H₂O to back exchange the amide and hydroxyl hydrogens to give the desired CMT-4-d6 (37).

Example 27

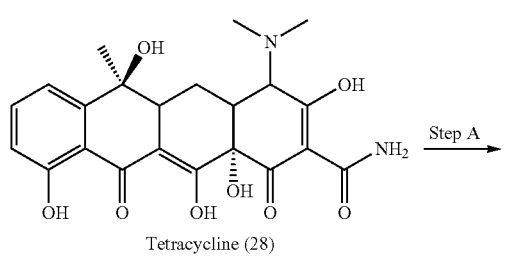

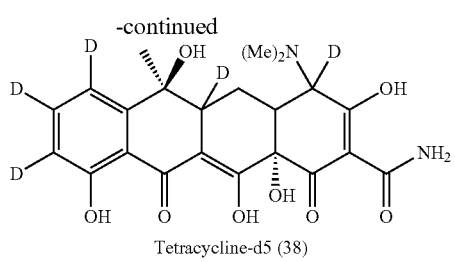

Step A

If one were to follow the method of Yoshida and coworkers (Yoshida, T.; et al. Journal of the American Chemical Society, 101(8), 2027-2038, 1979), Tetracycline (28) can be treated with Palladium on carbon in the presence of hydrogen and deuterated water and heated to give the resulting deuterated Tetracylcine-d12. Tetracylcine-d12 can then be treated with H₂O to back exchange the readily exchangeable amide and hydroxyl hydrogens to give the desired Tetracylcine-d5 (38).

Example 28

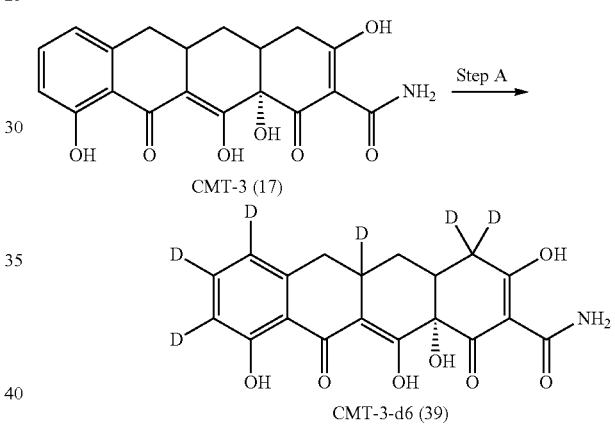

Step A

If one were to follow the method of Yoshida and coworkers (Yoshida, T.; et al. Journal of the American Chemical Society, 101(8), 2027-2038, 1979), compound (17) can be treated with Palladium on carbon in the presence of hydrogen and deuterated water and heated to give the resulting deuterated Tetracycline-d12. Tetracycline-d12 can then be treated with H₂O to back exchange the readily exchangeable amide and hydroxyl hydrogens to give the desired Tetracylcine-d6 (39).

Example 29

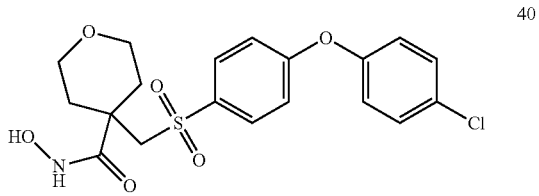 [SMILES: O=C(NO)C1(CS(=O)(=O)c2ccc(Oc3ccc(Cl)cc3)cc2)CCOCC1]

N-hydroxy-4-([4-[4-chlorophenoxy]benzenesulfonyl]methyl)-2,3,5,6-tetrahydropyran 4-carboxamide (40) (also identified as RO113-0830 or CTS-1027) can be synthesized via standard literature procedures (Fisher, Lawrence E.; Dvorak, Charles; Green, Keena; Janisse, Samantha; Prince, Anthony; Sarma, Keshab; McGrane, Paul; Moore, David; Campbell, Jeffrey; Baptista, Janel; Broka, Chris; Hendricks, Than; Walker, Keith; Yee, Calvin *From Bench to Pilot Plant. ACS Symposium Series*, Vol. 817, Chapter 6, (Apr. 19, 2002), pages 89-100 and references within).

Example 105

In-vitro Assay for Determining Microsomal Stability of Select Compounds in Human and Mouse Microsomes Human and mouse microsomal stability was determined for select compounds following the method of Houston (Houston, J B; Biochem. Pharmacol. 47, (1994), 1469).

1 µM concentration of compound and seperate human and mouse microsomes (0.3 mg/mL, BD bioscience) were used in the in-vitro assay. To ensure proper energy supply for microsomal degradation of compound, an energy regenerating system comprised of 100 mM potassium phosphate, 2 mM NADPH, 3 mM $MgCl_2$, pH=7.4. and the microsomal protein is added to each sample and the resulting suspension is then incubated in duplicate for 60 min at 37° C. in a rotary shaker. A control is run for each test agent in duplicate omitting NADPH to detect NADPH-free degradation. At T=0 and T=60 min., an aliquot is removed from each experimental and control reaction and then mixed with an equal volume of ice-cold Stop Solution (consisting of 0.3% acetic acid in acetonitrile containing haloperidol and diclofenac as internal standards). Stopped reactions are then incubated for at least ten minutes at −20° C., and an additional volume of water is then be added. The samples are then centrifuged to remove precipitated protein, and the supernatants are then analyzed by LC-MS/MS to determine the percentage of compound remaining. The LC-MS/MS system used was an Agilent 6410 mass spectrometer coupled with an Agilent 1200 HPLC and a CTC PAL chilled autosampler, all controlled by MassHunter software (Agilent), or an ABI2000 mass spectrometer coupled with an Agilent 1100 HPLC and a CTC PAL chilled autosampler, all controlled by Analyst software (ABI). After separation on a C18 reverse phase HPLC column (Agilent, Waters, or equivalent) using an acetonitrile-water gradient system, peaks were analyzed by mass spectrometry (MS) using ESI ionization in MRM mode.

Table 1 and 2 below show the microsomal stability of select compounds in both human and mouse microsomes.

TABLE 1

In-vitro Human Microsomal Stability Of Select Compounds

| Compound ID # | Compound Concentration (microMoles) | Test Species | Mean Remaining Parent with NADPH (%)[1] | Mean Remaining Parent without NADPH (%)[1] |
|---|---|---|---|---|
| 5 | 1 | Human | 86 | 89 |
| 10 | 1 | Human | 88 | 97 |

[1]at T = 60 minutes

TABLE 2

In-vitro Mouse Microsomal Stability Of Select Compounds

| Compound ID # | Compound Concentration (microMoles) | Test Species | % Mean Remaining Parent with NADPH (%)[1] | % Mean Remaining Parent without NADPH (%)[1] |
|---|---|---|---|---|
| 5 | 1 | Mouse | 83 | 88 |
| 10 | 1 | Mouse | 85 | 91 |

[1]at T = 60 minutes

Measuring Neuropathic Pain Inhibition-(SNL)-Mouse Animal Model:
Background and Description of the Animal Model To measure the neuropathic pain inhibiting affects of the MMP inhibitors of the present invention, the spinal nerve ligation (SNL) mouse model was run on a select number of compounds. This model which began with the work of Bennet and coworkers (Bennet, G. J. et al. Pain, 33, (1988), 87-107) and was optimized by Kim and Chung (Kim, S. H.; Chung, J. M. Pain, 50, (1992), 355-363) entails first, under magnification, the removal of one-third of the transverse process and then identifying and then dissecting free the L5 spinal nerve from the adjacent L4 spinal nerve in the mouse. The L5 spinal nerve is then tightly ligated using 6.0 silk suture. The nerve injury leads to hyperalgesia which manifests itself by enhanced responses to mechanical, heat and/or cooling stimuli. In this case, mechanical hyperalgesia is tested via Von Frey monofilaments in which filaments of varying thicknesses and bending force are individually applied to the plantar surface of the foot of the mouse. The threshold force necessary for paw withdrawal decreases dramatically after the nerve surgery. Potent pain inhibitors will reverse this affect resulting in greater force needing to be applied to cause the rodent paw to withdrawal.

Example 110

Intrathecal (i.t.) Administration of MMP Inhibitors in the (SNL)-Mouse Model of Pain Following preoperative baseline (Day −2) paw threshold measurement, FVB male mice were subjected to SNL injury (Day −1). The next day (Day 0) after SNL surgery, the animals were tested for post-operative baseline threshold measurements for mechanical allodynia; and the animals were then randomly assigned to one of 3 treatment groups (see Table 3). Over the course of the study, paw withdrawal threshold of these animals was measured in response to mechanical stimulation using the von Frey Monofilament Test.

To avoid systemic effects of the MMP inhibitors, the MMP inhibitors of the present invention were delivered into the cerebral spinal fluid (CSF) space around lumbosacral spinal cord via intrathecal (i.t.) administration, with the idea of targeting MMPs in the DRG, spinal cord, and spinal CSF. Intrathecal MMP inhibitor administration could then target not only spinal cord cells but also DRG cells. Each intrathecal (i.t.) injection was carried out according to the technique of Hylden and Wilcox (Hylden J L, Wilcox G L. Eur. J Pharmacol., 67, (1980), 313-6) 5.2 mg of each of the MMP inhibitors were first dissolved in 140 microliters of DMSO and then put into 1260 microliters of 0.5% hydroxypropyl cellulose (HPC) in water to make a fine suspension composed of compound in 10% DMSO-0.5% hydroxypropyl cellulose. 10 microliters of the mixture was injected into the intrathecal space of male FVB mice (weighing 22-25 grams each and obtained from the Jackson Laboratories, Bar Harbor, Me.), by lumbar puncture in a volume of 10 μl/mouse using a Hamilton microsyringe via a 30 gauge needle inserted between lumbar vertebrae 5 and 6. In brief, each animal was held firmly by the pelvic girdle in one hand, while the needle was inserted into the tissue on the right side of the L5 or L6 spinous process. The needle was moved forward and slipped into the groove between the spinous process and transverse process and gently moved forward to the intervertebral space at ~10° angle. As the needle was inserted (~0.5 cm) within the vertebral column a tail flick was evident, and the solution was then injected. Table 3 summarizes the various treatment groups and frequency of administration.

TABLE 3

Animal i.t. Treatment Groups & Compounds Tested

| Treatment | # of Mice | Dose | Route of Administration And Frequency |
|---|---|---|---|
| Vehicle | 8 | Group 1, 10 μl/mouse | i.t, daily injections, from day 1-6, starting day 1 |
| Compound # 5 | 4 | Group 2, 10 μl/mouse | i.t, daily injections, from day 1-6, starting day 1 |
| Compound # 10 | 5 | Group 3, 10 μl/mouse | i.t, daily injections, from day 1-6, starting day 1 |

*Vehicle = 10% DMSO, 0.5% hydroxypropyl cellulose in water

Tactile Allodynia Test. Mechanical allodynia was measured using the calibrated von Frey filaments (Semmes-Weinstein monofilaments; Stoelting, Wood Dale, Ill., U.S.A.). The plantar surface of the left injured paw of each animal was tested as described by Chaplan et al. (Journal of Neuroscience Methods, 53, (1994), 55-63). The Fifty percent paw withdrawal threshold response was determined by sequentially increasing or decreasing the stimulus strength according to the "up-down method" of Dixon (Annual Review Pharmacology Toxicology, 20, (1980), 441-462). For mice, eight von Frey filaments were used, with approximately equal logarithmic incremental bending forces (von Frey number: 1.65, 2.36, 2.44, 2.83, 3.22, 3.61, 3.84, 4.08, and 4.17; equivalent to 0.005, 0.02, 0.03, 0.07, 0.17, 0.41, 0.69, 1.20, and 1.48 g force, respectively).

Prior to testing, each animal was placed in a suspended clear plastic chamber with a wire mesh bottom and acclimated for 15 minutes. Testing was initiated with the 0.07 g (handle marking of 2.83) applied perpendicularly to the plantar surface of the affected hind paw; each filament was applied with enough pressure to cause a buckle effect. The absence of a paw lifting/withdrawal response after 6 s prompted the use of the next higher weight filament. Paw withdrawal, indicating a positive response, prompted the use of a weaker filament. After the initial positive response (i.e., paw withdrawal), the testing continued for four additional measurements, and was used to calculate the response threshold. Four consecutive positive responses received a score of 0.001 g, and five consecutive negative responses (i.e., no paw withdrawal) received a score of 1.5 g.

Analyses for Tactile Allodynia Testing. The 50% paw withdrawal threshold was calculated (PWT; Luo and Calcutt, J. Pharmacology Experimental Therapeutics, 303(3), (2002), 1199-1205; Chaplan et al. Journal of Neuroscience Methods, 53, (1994), 55-63) using the formula:

$$10(X_f + \kappa\delta)/10{,}000$$

where Xf is the final von Frey filament used (log units), κ is a value that analyzes the response pattern (taken from the table published by Chaplan et al., 1994), and δ is the mean difference between stimuli (log units).

Control of Bias. To prevent bias in the results of the study, the technical staff was not aware of the treatment history of each animal while evaluating the behavioral responses of the animals.

The results of the behavior testing which is presented in Table 4 clearly show the almost complete reversal of allodynia by compound #10 as compared to vehicle and compound #5.

TABLE 4

(i.t)-SNL-Mouse Behavioral Testing Results For Vehicle, Compounds #5 and #10

|  | Day (−2) Pre-operative Baseline[1] | Day 0 Postoperative Baseline[2] | Day 1[3] | Day 5 | Day 7 |
|---|---|---|---|---|---|
| Group 1: Vehicle | | | | | |
| Mean | 1.130 | 0.068 | 0.110 | 0.026 | 0.071 |
| Std. Dev. | 0.418 | 0.112 | 0.102 | 0.025 | 0.056 |
| Group 2: Compound #5 | | | | | |
| Mean | 1.265 | 0.050 | 0.098 | 0.079 | 0.190 |
| Std. Dev. | 0.271 | 0.048 | 0.100 | 0.055 | 0.230 |
| Group 3: Compound #10 | | | | | |
| Mean | 1.268 | 0.077 | 0.321 | 0.320 | 1.024 |
| Std. Dev. | 0.327 | 0.072 | 0.660 | 0.297 | 0.521 |

[1]Testing prior to SNL injury (pre-operative baseline)
[2]Testing 2 days after SNL injury (post operative injury baseline)
[3]Testing conducted 2 hr after first i.t. injection.

Example 111

Intraperitoneal (i.p.) Administration of MMP Inhibitors in the (SNL)-Mouse Model of Pain In order to better ascertain the bioavailability of the MMP compounds of the present invention when compound is administered outside of the spinal cord area, the SNL-mouse model was repeated with compounds #5 and #10 via intraperitoneal administration. Except for the mode of administration, number of mice/group and the number of injections and amount per injection of compound given, the rest of the study was done in the same manner (in regards to the surgeries and tactile allodynia testing and analysis) as Experiment 110. 3.2 mg of each of the MMP inhibitors #5 and #10 were dissolved in 320 microliters of DMSO. To the solution was then added 32 microliters of Tween 80, followed by 2850 microliters of phosphate buffered saline (PBS). This gave a final concentration of 10% DMSO, 1% Tween and 1 mg/ml compound. 0.1 ml of this solution was then injected per mouse/day (for five consecutive days) to give an approximate dose of 3.3 mg/Kg. The treatment groups are outlined in Table 5. The results of the behavior tests can be seen in Table 6. It is clear that compound #10 shows a complete reversal of mechanical allodynia by day 5. It is interesting to point out the rather prolonged effect exerted by compound #10 even after 48 hours (day 6) from the last injection (day 4).

TABLE 5

Animal IP Treatment Groups

| Treatment | # of mice | Dose | Route of Administration And Frequency |
|---|---|---|---|
| Vehicle | 3 | Group 1, 100 µl/mouse | IP daily injections day 1-5 |
| Compound # 5 | 3 | Group 2, 100 µl/mouse | IP daily injections day 1-5, starting day 1 |
| Compound #10 | 3 | Group 3, 100 µl/mouse | IP daily injections day 1-5, starting day 1 |

*Vehicle = 10% DMSO, 1% Tween 80, in PBS.

TABLE 6

(i.p.)-SNL-Mouse Behavioral Testing Results For Vehicle, Compounds #5 and #10

|  | Day 0 Postoperative Baseline | Day 1 | Day 2 | Day 5 | Day 6 | Day 7 |
|---|---|---|---|---|---|---|
| Group 1: Vehicle |  |  |  |  |  |  |
| Mean | 0.112 | 0.167 | 0.137 | 0.130 | 0.065 | 0.056 |
| Std. Dev. | 0.078 | 0.098 | 0.142 | 0.056 | 0.048 | 0.019 |
| Group 2: Compound #5 |  |  |  |  |  |  |
| Mean | 0.046 | 0.078 | 0.117 | 0.238 | 0.099 | 0.128 |
| Std. Dev. | 0.065 | 0.046 | 0.127 | 0.246 | 0.113 | 0.098 |
| Group 3: Compound #10 |  |  |  |  |  |  |
| Mean | 0.096 | 0.170 | 0.350 | 1.470 | 0.867 | 0.250 |
| Std. Dev. | 0.059 | 0.192 | 0.226 | 0.052 | 0.553 | 0.118 |

Example 120

Measuring Inflammatory Pain Inhibition- Carrageena (CARR)- Induced Inflammation in Rats If one were to measure the inflammatory pain inhibiting affects of the MMP inhibitors of the present invention, one could use the Carrageenan model for measuring neuropathic pain as presented in LaBuda, C. J., and Fuchs, P. N. Neuroscience Letters, 304, (2001), 137-140.

Acute Model: Subcutaneous injection into the hindpaw of a rat: An acute inflammatory condition is produced by a subcutaneous injection of 3% lambda Carrageenan (0.12 ml) into the plantar surface of one hindpaw under light isoflurane anesthesia. Usually, there is an additional control group that receives an equal volume of saline. Animals would then receive the MMP inhibitors of the present invention 3½ hours after the CARR injection, Quantification of pain behavior could then be performed via the paw withdrawal animal model using the same procedures as outlined in Experiment 110 & 111.

Chronic Model: Intra-articular injection. A longer lasting state of inflammation is produced by performing intra-articular injection of CARR (0.1 ml, 3%) into the tibial joint under isoflurane anesthesia. This route of administration induces an inflammatory condition that can last for up to 7 days following injection and is an established model of arthritic inflammatory pain. Quantification of pain behavior could then be performed using the same procedures as outlined in Experiments 110 & 111.

Example 125

Morphine Tolerance & Naloxone-Precipitated Morphine Withdrawal Mouse Studies

One can measure the effects of intrathecal (i.t.) or intraparitoneal (i.p.) administration of a matrix metallorproteinase (MMP) inhibitor in a mouse model of morphine analgesia, tolerance and withdrawal. The purpose of which is to measure the effects of a MMP inhibitor on 1) attenuating morphine tolerance in mice and 2) withdrawal behavior in naloxone-precipitated morphine withdrawal in mice. Based on the work of Song and coworkers, (The Journal of Neuroscience, 30(22), (2010), 7613-7623) one can utilize adult male and female CD-1 mice (Charles River Laboratories) and wild-type (WT) FVB mice (The Jackson Laboratory) weighing 24-28 g at 8-10 weeks of age. According to the work of Song and coworkers, a hot plate apparatus can be used for the pain threshold and morphine analgesia/tolerance tests. A cutoff time of 30 s can be set to avoid tissue damage. Adult Kunming (KM) mice can also be used as an added confirmation of the behavioral effects of administering a matrix metalloproteinase-2 and -9 inhibitor on other strains of mice.

Drug Administration: The matrix metalloproteinase (MMP) inhibitors can be dissolved in phosphate buffered saline (PBS) or dimethylsulfoxide (DMSO) and diluted in PBS (final concentration of DMSO for intrathecal administration was 10%). Optimally the MMP inhibitor can first be dissolved in DMSO and then diluted up in PBS and 1% tween to give a final concentration of 10% DMSO, 1% Tween in PBS buffer. Administration of the MMP inhibitors (5-10 µg) and the vehicle controls PBS and DMSO can be done by injecting them intrathecally (IT) (each in 10 µl), respectively, under brief inhalation of anesthesia for ~5 min after each morphine injection, by means of lumbar puncture at the intervertebral space of L4-5 and L5-6 for multiple injections, using a stainless steel needle (30 gauge) attached to a 25 µl Hamilton syringe.

Morphine withdrawal Studies. Based on the work of Zachariou and coworkers (Zachariou V, Georgescu D, Sanchez N, Rahman Z, DiLeone R, Berton O, Neve R L, Sim-Selley L J, Selley D E, Gold S J, Nestler E J Proc Natl Acad Sci USA, Vol. 100 (1003), p. 13656-13661) as well as the work of Liu and coworkers (Liu W T, Li H C, Song X S, Huang Z J, Song X J , FASEB J 23, (2009), p. 90-98), mice can be repeatedly injected with morphine in seven escalating doses every 8 h (20, 40, 60, 80, 100, 100, and 100 mg/kg, i.p.). Two hours after the last morphine injection, mice can be injected with naloxone (1 mg/kg, s.c.), and withdrawal symptoms then can be monitored for 30 min after naloxone administration. Naloxone is a µ-opioid receptor competitive antagonist that can be used to counter the effects of the morphine in the mouse and to initiate morphine withdrawal symptoms.

MMP inhibitor effects on morphine withdrawal For testing the morphine withdrawal-like behavioral signs following intrathecal MMP inhibitor administration, the withdrawal symptoms can be monitored for 30 min 1-2 h after naloxone administration. In addition to measuring individual withdrawal signs, an overall opiate withdrawal score can be calculated using a calculation taken from the work of Song and coworkers (The Journal of Neuroscience, 30(22), (2010), 7613-7623) as well as others (Zachariou et al., 2003; Liu et al., 2009a) (no. of backward walking steps×0.1)+(diarrhea× 2)+(no. of jumps×0.1)+(paw tremor×0.1)+ptosis+tremor+(% weight loss×5)+no. of wet-dog shakes.

MMP inhibitor effects on attenuating morphine pain blocking. To test the effects of MMP inhibitors on the pain threshold and the initial analgesic response to morphine, mice can be placed on a 55° C. hot plate apparatus and the latency to lick a paw measured. Data can be calculated as the percentage maximal possible effect (MPE %), which can be calculated by using the formula from Song and coworkers (The Journal of Neuroscience, 30(22), (2010), 7613-7623) (the following formula: 100×[(drug response time−basal response time)/(30 s−basal response time)]=MPE %. Morphine (10 mg/kg, s.c.), MMP inhibitor (5-10 µg, i.t.) and the control vehicles PBS and DMSO (1%, i.t.) can be administered 30 min before testing. The protocol would be the same as that described by the groups of Song et al., Zachariou et al. and Liu et al. To evaluate the physical tolerance to morphine each mouse can be placed on a 55° C. hot plate apparatus, and the latency to lick a paw measured following subcutaneous morphine injection. For testing acute tolerance, the latency to lick a paw can be measured at 0.5, 1, 1.5, and 2 h after a single dose of morphine at 10 mg/kg, administered 24 h after a morphine treatment at 100 mg/kg. Chronic tolerance can be tested following repetitive treatment of morphine at 10 mg/kg given daily for 7 days, and the analgesic effect measured 30 min after each injection.

Example 130

Assay for Determining MMP-2 Inhibition

MMP-2 inhibitor activity was carried out via the method of Knight (Knight, C. G. et. al, *FEBS LETT.* 296 (3), (1992), 263-266), using an assay buffer comprised of 50 mM Tris-HCl, pH 7.6, 200 mM NaCl, 5 mM $CaCl_2$ and 1 µM $ZnSO_4$. A concentration of MMP inhibitor of the present invention was tested (1 microMolar) in duplicate runs. Catalytic domain of MMP-2 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was then started by the addition of 10 µM of fluorescent substrate Mca-P-L-G-L-Dpa-A-R-NH2 (Kd~8 microMolar)[SEQ ID NO: 1]. The fluorescent product, McaPLG, was then measured at excitation of 355 nm and emission 405 nm by an automatic plate multireader at 37° C. A positive control was separately run using the broad spectrum MMP inhibitor GM6001 as a control compound (MMP-2 IC50=0.5 nanoMolar). Table 7 summarizes the results of the inhibition study.

TABLE 7

Percent MMP-2 Inhibition

| Compound ID# | Compound Concentration | Substrate | Substrate Concentration | Average Percent Inhibition |
|---|---|---|---|---|
| 5 | 1 microMolar | Mca-P-L-G-L-Dpa-A-R-NH2 [SEQ ID NO: 1] | 10 microMolar | 97% |
| 10 | 1 microMolar | Mca-P-L-G-L-Dpa-A-R-NH2 [SEQ ID NO: 1] | 10 microMolar | 96% |

Example 131

Assay for Determining MMP-9 Inhibition

MMP-9 inhibitor activity was carried out via the method of Bickett, D. M.; (Bickett, D. M., et al *Analytical Biochemistry* 212, (1993), 58-64), using an assay buffer comprised of 50 mM Tris-HCl, pH 7.6, 200 mM NaCl, 5 mM $CaCl_2$ and 1 µM ZnSO4. A concentration of MMP inhibitor of the present invention was tested (1 microMolar) in duplicate runs. Catalytic domain of MMP-9 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was started by the addition of 10 µM of fluorescent substrate DNP-Pro-Cha-Gly-Cys(Me)-His-Ala-Lys(n-Me-Abz)-NH2 [SEQ ID NO: 1][Cha=β-cyclohexylalanyl; Abz=2-aminobenzoyl(anthraniloyl)] (Kd~7 microMolar). The fluorescent product, Dnp-PChaG, was then measured at excitation of 365 nm and emission 450 nm by an automatic plate multireader at 37° C. A positive control was separately run using the broad spectrum MMP inhibitor GM6001 as a control compound (MMP-9 IC50=0.2 nanoMolar). Table 8 summarizes the results of the inhibition study.

TABLE 8

Percent MMP-9 Inhibition

| Compound ID# | Compound Concentration | Substrate | Substrate Concentration | Average Percent Inhibition |
|---|---|---|---|---|
| 5 | 1 microMolar | DNP-Pro-Cha-Gly-Cys(Me)-His-Ala-Lys(N-Me-Abz)-NH2 [SEQ ID NO: 1] | 10 microMolar | 82% |
| 10 | 1 microMolar | DNP-Pro-Cha-Gly-Cys(Me)-His-Ala-Lys(N-Me-Abz)-NH2 [SEQ ID NO: 1] | 10 microMolar | 78% |

Example 132

Assay for Determining MMP-1 Inhibition

If one were interested in measuring the MMP-1 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 µM ZnSO4 is used. A single concentration could be tested (i.e., 1 microMolar) in duplicate runs. Catalytic domain of MMP-1 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 µM of fluorescent substrate DNP-Pro-Cha-Gly-Cys(Me)-His-Ala-Lys(N-Me-Abz)-NH2 [SEQ ID NO: 1] [Cha=β-cyclohexylalanyl; Abz=2-aminobenzoyl(anthraniloyl)] (10 µM). The fluorescent product, DnpPChaG, could then be measured at an excitation wavelength of 365 nm and emission wavelength of 450 nm using an automatic plate multireader at 37° C. A positive control could also be run separately using the broad spectrum MMP inhibitor Tyr-hydroxamic acid as a control compound.

Example 133

Assay for Determining MMP-7 Inhibition

If one were interested in measuring the MMP-7 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 µM ZnSO4 is used. A single concentration could be tested (i.e., 1 microMolar) in duplicate runs. Catalytic domain of MMP-7 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 µM of fluorescent substrate Mca-P-L-G-L-Dpa-A-R-NH2 [SEQ ID NO: 1]. The fluorescent product, McaPLG, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

Example 134

Assay for Determining MMP-3 Inhibition

If one were interested in measuring the MMP-3 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 µM ZnSO4 is used. A single concentration could be tested (i.e., 1 microMolar) in duplicate runs. Catalytic domain of MMP-3 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 µM of fluorescent substrate McaRPK-PVENvalWRK(Dnp)NH2 [SEQ ID NO: 1]. The fluorescent product, McaRPK, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

Example 135

Assay for Determining MMP-12 Inhibition

MMP-12 inhibitor activity can be carried out by first separating the cleaved and uncleaved substrates by charge via electrophoretic mobility shift and then measuring the fluorescence of the separated products and comparing them with control reactions to determine inhibition of enzyme activity. One could then run the MMP-12 assay using an assay buffer comprised of 100 mM HEPES, pH 7.5, 0.01% Brij-35, 1.5 mM NaCl and 2 mM $CaCl_2$. A single inhibitor concentration could be tested (i.e. 1 microMolar) in duplicate runs. The reaction could be started by first the addition of substrate and then incubating the reaction mixture for 1 hour at room temperature. The reaction could then be terminated via the addition of a stop buffer consisting of 100 mM HEPES (pH 7.5), 30 mM EDTA, 0.015% Brij-35, and 5% DMSO. A positive control could then be run separately using the broad spectrum MMP inhibitor GM6001 as a control compound.

Example 136

Assay for Determining MMP-13 Inhibition

If one were interested in measuring the MMP-13 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 µM ZnSO4 is used. A single concentration could be tested (i.e., 1 microMolar) in duplicate runs. Catalytic domain of MMP-13 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 µM of fluorescent substrate Mca-P-L-G-L-Dpa-A-R-NH2 [SEQ ID NO: 1]. The fluorescent product, McaPLG, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

---

What is claimed is:

1. A method of treating an MMP mediated condition, comprising orally administering to a subject an effective amount of a compound of Formula 5 or 10:

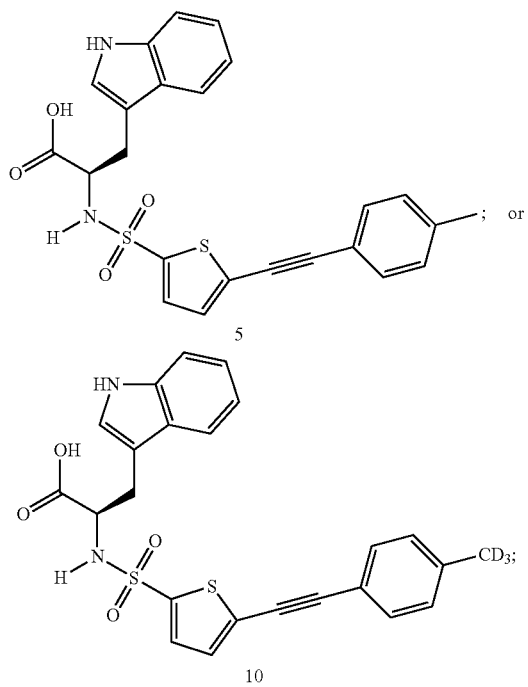

including N-oxides, pharmaceutically acceptable salts, formulations, polymorphs, tautomers, racemic mixtures and stereoisomers thereof; and the MMP mediated condition is selected from enhanced or exaggerated sensitivity to pain; acute pain; burn pain; atypical facial pain; neuropathic pain; back pain; complex regional pain syndromes I and II; arthritic pain; sports injury pain; pain related to viral infection; phantom limb pain; cancer pain; post-operative pain; nociceptive pain; inflammatory pain; visceral pain; neuropathic pain; neuralgia; neuropathy related to diabetes; hyperalgesia and withdrawal pain related to use of narcotics.

2. The method of claim 1, wherein said enhanced or exaggerated sensitivity to pain is selected from the group consisting of hyperalgesia, causalgia and allodynia.

3. The method of claim 1, wherein said pain related to viral infection is selected from the group consisting of HIV pain, post-polio syndrome and post-herpetic neuralgia.

4. The method of claim 1, wherein said visceral pain is selected from the group consisting of angina, irritable bowel syndrome (IBS) and inflammatory bowel disease.

5. A method of treating pain derived from an MMP mediated disease, comprising orally administering to a subject an effective amount of a compound of Formula 5 or 10:

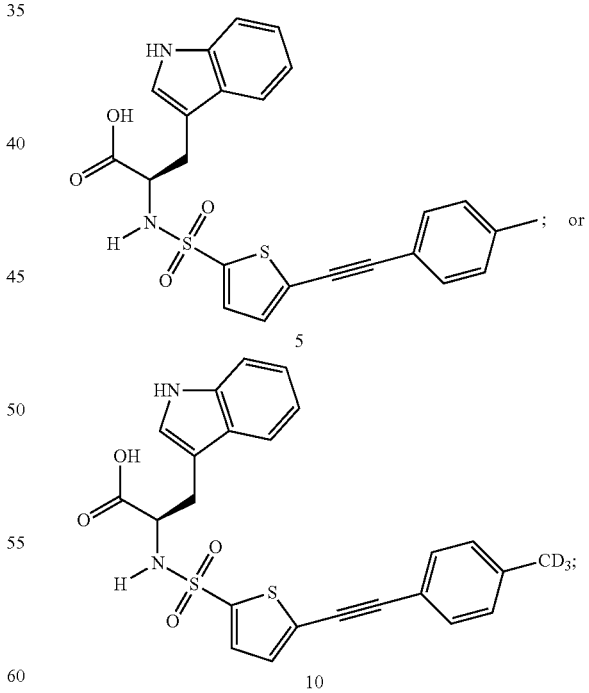

including N-oxides, pharmaceutically acceptable salts, formulations, polymorphs, tautomers, racemic mixtures and stereoisomers thereof; and the MMP mediated disease is selected from rheumatoid arthritis, osteoarthritis, diabetes, shingles, multiple sclerosis, bacterial infections, diabetic retinopathy, HIV, spinal injury, trigeminal neuralgia, periodontis, inflammatory and fibrotic syndromes, intestinal bowel syndrome, gingivitis, corneal epidermal and gastric ulceration, viral infection, morphine tolerance, drug addiction and withdrawl.

6. The method according to claim 1, wherein the condition is neuropathic pain.

7. The method according to claim 1, wherein the condition is osteoarthritic pain.

8. The method according to claim 1, wherein the condition is inflammatory pain.

* * * * *